(12) United States Patent
Stein et al.

(10) Patent No.: US 10,682,093 B1
(45) Date of Patent: *Jun. 16, 2020

(54) DIGITAL PLATFORM TO IDENTIFY HEALTH CONDITIONS AND THERAPEUTIC INTERVENTIONS USING AN AUTOMATIC AND DISTRIBUTED ARTIFICIAL INTELLIGENCE SYSTEM

(71) Applicant: Spiral Physical Therapy, Inc., Del Mar, CA (US)

(72) Inventors: Spencer Stein, Del Mar, CA (US); Stephen Moxey, Carlsbad, CA (US); Lee Stein, Del Mar, CA (US)

(73) Assignee: Spiral Physical Therapy, Inc., Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/396,411

(22) Filed: Apr. 26, 2019

Related U.S. Application Data

(63) Continuation of application No. 16/228,169, filed on Dec. 20, 2018, now Pat. No. 10,327,697.

(51) Int. Cl.
*G06K 9/00* (2006.01)
*A61B 5/00* (2006.01)
(Continued)

(52) U.S. Cl.
CPC ............ *A61B 5/486* (2013.01); *A61B 5/0064* (2013.01); *A61B 5/1071* (2013.01);
(Continued)

(58) Field of Classification Search
CPC .................................................. A61B 5/7267
See application file for complete search history.

(56) References Cited

U.S. PATENT DOCUMENTS 7,007,813 B2    7/2006  Grace
7,077,813 B2 *  7/2006  Grace .................... A61B 5/103
                                                          600/594
(Continued)

FOREIGN PATENT DOCUMENTS

CN    105825062 A    8/2016
RU    2 607 187 C1   1/2017

OTHER PUBLICATIONS

Rehm et al ("3D-model of spine using EOS imaging system, Inter-reader reproducibility and reliability", PLOS ONE | DOI:10.1371/journal.pone.0171258 Feb. 2, 2017, p. 13 (Year: 2017).*

(Continued)

*Primary Examiner* — Oneal R Mistry
(74) *Attorney, Agent, or Firm* — Brinks Gilson & Lione

(57) ABSTRACT

This disclosure is directed to method and system for automatic, distributed, computer-aided, and intelligent data collection/analytics, health monitoring, health condition identification, and patient preventive/remedial health advocacy. The system integrates (1) distributed patient health data collection devices, (2) centralized or distributed data servers running various intelligent and predictive data analytics engines for health screening, assessment, patient health condition identification, and patient preventive/remedial health advocacy, 3) specifically designed data structures including quantized health indicator vectors, patient health condition identification matrices and patient health condition vectors, (4) portal servers configured to interface with (5) distributed physician terminal devices and (6) distributed patient terminal devices for delivering health condition identification, health interventions and patient preventive/remedial health advocacy, and for monitoring and tracking patient activities. The various intelligent and predictive engines are configured to learn and extract hidden features (Continued)

and correlations from a large amount of data obtained from the distributed data collection devices.

20 Claims, 35 Drawing Sheets

(51) Int. Cl.
  *A61B 5/11* (2006.01)
  *A61B 5/107* (2006.01)
  *G16H 50/30* (2018.01)
  *G16H 30/40* (2018.01)
  *G16H 10/60* (2018.01)
  *G06K 9/66* (2006.01)

(52) U.S. Cl.
  CPC .......... *A61B 5/1075* (2013.01); *A61B 5/1114* (2013.01); *A61B 5/1116* (2013.01); *A61B 5/7475* (2013.01); *G06K 9/66* (2013.01); *G16H 10/60* (2018.01); *G16H 30/40* (2018.01); *G16H 50/30* (2018.01); *A61B 5/7267* (2013.01); *A61B 5/7435* (2013.01)

(56) References Cited

U.S. PATENT DOCUMENTS

| | | | |
|---|---|---|---|
| 7,335,167 | B1 | 2/2008 | Mummy |
| 8,715,176 | B2 | 5/2014 | Lemme |
| 10,019,520 | B1 | 7/2018 | Muske |
| 2002/0136437 | A1 | 9/2002 | Gerard et al. |
| 2013/0207889 | A1* | 8/2013 | Chang .................. A61B 5/0002 345/156 |
| 2015/0223730 | A1* | 8/2015 | Ferrantelli ........... A61B 5/1072 600/476 |
| 2018/0052961 | A1 | 2/2018 | Shrivastava et al. |
| 2018/0108432 | A1 | 4/2018 | Slater |
| 2018/0168516 | A1 | 6/2018 | Pappada et al. |

OTHER PUBLICATIONS

Hui, Xiaonan et al., "Monitoring vital signs over multiplexed radio by near-field coherent sensing," School of Electrical and Computer Engineering, Cornell University, Ithaca, New York, https://doi.org/10.1038/s41928-017-0001-0, *Nature Electronics*, www.nature.com/natureelectronics, 2017 (5 pp.).

* cited by examiner

1600 — Measured Front-View Postural Deviations / Measured Side-View Postural Deviations

| Patients | Head Shift | Head Tilt | Shoulder Shift | Shoulder Tilt | Underbust Shift | Underbust Tilt | Hip Shift | Hip Tilt | Knee Shift | Knee Tilt | Head Shift | Shoulder Shift | Hip Shift | Knee Shift |
|---|---|---|---|---|---|---|---|---|---|---|---|---|---|---|
| Patient 1 | -0.09 | 3.41 | -0.05 | 0.95 | -0.09 | 2.34 | -0.1 | 0.3 | -0.05 | 0 | 1.9 | 3.18 | 1.4 | 0.84 |
| Patient 2 | -0.09 | 3.41 | -0.05 | 1.1 | -0.09 | 2.34 | -0.1 | 0.3 | -0.05 | 0 | 1.9 | 3.18 | 1.4 | 0.84 |
| Patient m-1 | -0.23 | -0.8 | -0.47 | -0.78 | -0.56 | 5.18 | -1.3 | 1.8 | -0.71 | 0 | 0.23 | 0.85 | 2.56 | 1.69 |
| Patient m | 0 | 0.71 | -0.45 | 1.27 | -0.33 | -1.31 | -0.1 | 0.6 | 0 | 2.92 | 2.43 | 1.63 | 1.13 | 0.6 |

1602 — Front-View Postural Deviation Quantization Table / Side-View Postural Deviation Quantization Table

| Quantization Levels | Head Shift | Head Tilt | Shoulder Shift | Shoulder Tilt | Underbust Shift | Underbust Tilt | Hip Shift | Hip Tilt | Knee Shift | Knee Tilt | Head Shift | Shoulder Shift | Hip Shift | Knee Shift |
|---|---|---|---|---|---|---|---|---|---|---|---|---|---|---|
| -2 | | | | | | | | | | | | | | |
| -1 | | | | | | | | | | | | | | |
| 0 | | | | | | | | | | | | | | |
| 1 | | | | | | | | | | | | | | |
| 2 | | | | | | | | | | | | | | |

1604 — Quantized Front-View Postural Deviations / Quantized Side-View Postural Deviations

| Patients | Head Shift | Head Tilt | Shoulder Shift | Shoulder Tilt | Underbust Shift | Underbust Tilt | Hip Shift | Hip Tilt | Knee Shift | Knee Tilt | Head Shift | Shoulder Shift | Hip Shift | Knee Shift |
|---|---|---|---|---|---|---|---|---|---|---|---|---|---|---|
| Patient 1 | 0 | 2 | 0 | 1 | 0 | 0 | 0 | 0 | 0 | 2 | 1 | 1 | 1 | 0 |
| Patient 2 | 0 | 1 | 0 | 1 | -1 | 0 | 0 | 0 | 0 | 2 | 1 | 2 | 1 | 0 |
| Patient m-1 | 0 | 0 | 0 | -1 | 0 | 2 | 0 | 2 | 2 | 1 | 1 | 1 | 2 | 0 |
| Patient m | 0 | 0 | 0 | 2 | 0 | 0 | 0 | 0 | 1 | 2 | 0 | 2 | 2 | 0 |

Figure 16

| Measurement | Result | Trend | Comparison |
|---|---|---|---|
| Shoulder Left To Elbow Length | 14.80 | > | ◄ |
| Shoulder Right To Elbow Length | 12.80 | > | ◄ |
| Knee Left Height | 20.80 | > | ◄ |
| Knee Right Height | 20.90 | > | ◄ |
| Thigh Mid Left Girth | 22.90 | > | ◄ |
| Thigh Mid Right Girth | 23.10 | > | ◄ |
| Calf Left Girth | 18.70 | > | ◄ |
| Calf Right Girth | 18.90 | > | ◄ |
| Biceps Left Girth | 15.90 | > | ◄ |
| Biceps Right Girth | 15.90 | > | ◄ |
| Chest At Blades Girth | 47.80 | > | ◄ |
| Bust Girth | 47.50 | > | ◄ |
| Neck To Underbust Volume | 26996.60 | > | ◄ |
| Underbust To Waist Volume | 17010.20 | > | ◄ |
| Neck Collar Girth | 17.10 | > | ◄ |

2402 — 2404 — 2406 — 2408

| Measurement | Result | Trend | Comparison |
|---|---|---|---|
| Weight Front Right | 36.90 | > | ◄ |
| Weight Front Left | 46.80 | > | ◄ |
| Weight Back Left | 0.80 | > | ◄ |
| Weight Back Right | 0.20 | > | ◄ |
| Hips At Width Max Girth | 46.10 | > | ◄ |
| Seat Girth | 44.80 | > | ◄ |
| Outseam Left Angled | 44.10 | > | ◄ |
| Outseam Right Angled | 44.20 | > | ◄ |
| Waist Should Back Height Left | 44.80 | > | ◄ |
| Waist Should Back Height Right | 44.80 | > | ◄ |
| Waist To Seat Right | 0.20 | > | ◄ |
| Waist To Seat Left | 0.80 | > | ◄ |
| Mid Shoulder Left To Underbust | 11.10 | > | ◄ |
| Mid Shoulder Right To Underbust | 11.80 | > | ◄ |
| Ankle Right Height Outside | 3.90 | > | ◄ |
| Ankle Left Height Outside | 8.10 | > | ◄ |

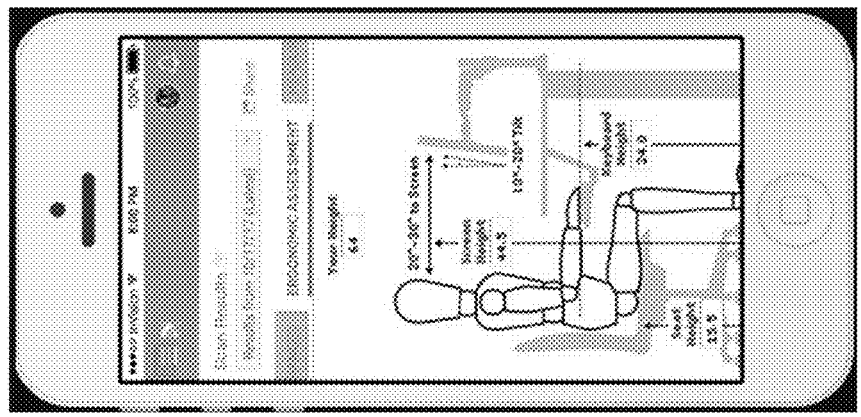
Figure 30

US 10,682,093 B1

DIGITAL PLATFORM TO IDENTIFY HEALTH CONDITIONS AND THERAPEUTIC INTERVENTIONS USING AN AUTOMATIC AND DISTRIBUTED ARTIFICIAL INTELLIGENCE SYSTEM

CROSS-REFERENCE TO RELATED APPLICATION

This application is a continuation of U.S. application Ser. No. 16/228,169, filed Dec. 20, 2018, pending, the entirety of which is hereby incorporated by reference herein.

TECHNICAL FIELD

This disclosure relates to an automated and distributed platform for computer-aided health screening, health risk assessment, disease intervention, patient health condition identification, health advocacy, and health monitoring.

BACKGROUND

Many healthcare providers rely on visual interpretation of a patient during a health assessment. For example, identifying abnormal posture or central adiposity are often assessed visually. It is important to distinguish between types of abnormal posture, such as scoliosis, pelvic twists, or lower cross syndrome for predicting health risks, prognostication, and effective intervention/therapy matching. Patient health data (PHD) is ordinarily collected and processed onsite in centralized medical centers, hospitals, clinics, and medical labs. The collected data are ported to electronic medical record systems to be examined and analyzed by physicians and other medical professionals for further health screening, health risk assessment, disease prevention, patient health condition identification (PHCI), and patient preventive/remedial health advocacy (PPRHA). Patient preventive/remedial healthy advocacy may be alternatively referred to as patient therapeutic interventions. The term "therapeutic" is used herein to broadly refer to prescriptive or nonprescriptive medicine, supplements, self-directed management, at-home care, therapies, medical/biological tests, referrals, and the like based on the patient health conditions. Often, patient health data collection and health assessment require in-person clinic or hospital visits by patients. Visual assessment of the human body carries inconsistency, lack of reproducibility, and requires access to a healthcare provider, which is not always possible in rural or underserved populations and often produce findings that can be inconsistent and difficult to reproduce. Alternatively, taking measurements by hand using measuring tape and a goniometer provides objective data, but is a very time consuming process. However, the same issues of inconsistency, lack of reproducibility, and requirements of access to a healthcare provider remain the same using handheld measuring tools. Additionally, manual anthropometric measurements such as measurements of girth or posture measurements have been shown to vary in precision and have poor inter and intra-actor reliability.

SUMMARY

This disclosure describes an automatic, distributed, computer-aided, and intelligent system and platform for health monitoring and data collection/analytics. The system integrates (1) distributed PHD collection servers and devices, (2) centralized or distributed data servers running various intelligent and predictive data analytics engines for health screening, risk assessment, PHCI and PPRHA, (3) specifically designed data structures including quantized health indicator vectors, a quantized PHCI matrix, and patient health condition vectors, (4) portal servers configured to interface with (5) distributed physician terminal devices, and (6) distributed patient terminal devices for receiving health evaluations, delivering interventions and PPRHA items, and for monitoring and tracking patient activities. The system disclosed herein is based on computer technologies and designed to use artificial intelligence tools to solve technical problems in computer-aided health screening, risk assessment, PHCI, and PPRHA.

BRIEF DESCRIPTION OF THE DRAWINGS

FIG. 16 shows exemplary health indicator vectors and their quantization using a quantization table.

FIGS. 20-26 illustrate exemplary graphical user interfaces on a physician terminal device for accomplishing physician functions in the system of FIG. 1.

FIGS. 27-31 illustrate exemplary graphical user interfaces on a patient terminal device for accomplishing patient tracking, monitoring, and other functions in the system of FIG. 1.

DETAILED DESCRIPTION

Figure 1:
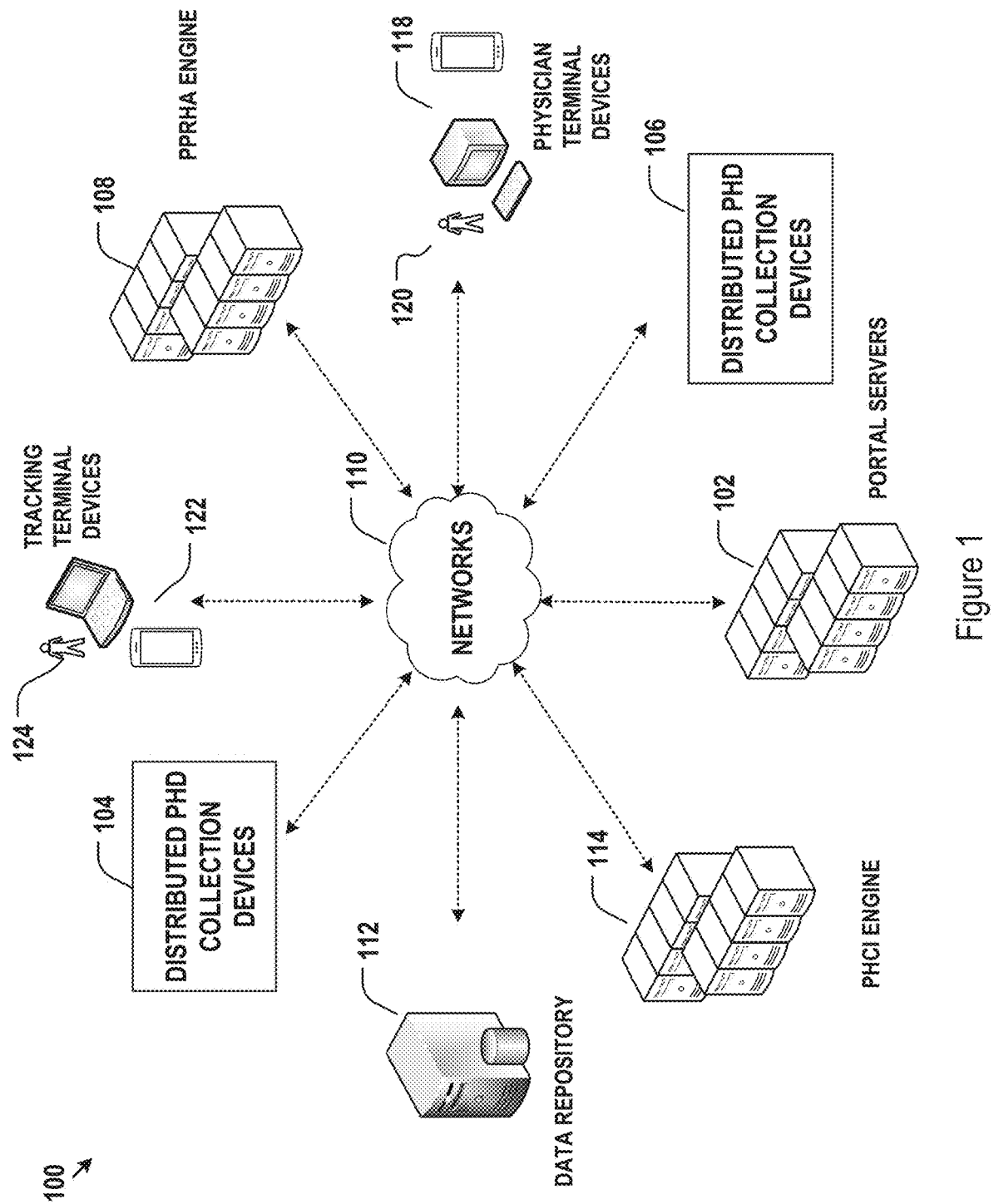
FIG. 1 illustrates an exemplary distributed data processing system for automatic and intelligent PHD collection/analytics, health screening, risk assessment, disease intervention, PHCI, PPRHA, and patient monitoring.

Health screening, health risk assessment, disease intervention, patient health condition identification (PHCI), and patient predictive/remedial health advocacy (PPRHA) traditionally rely on manual examination, by physicians, utilizing PHD for an individual patient collected at physically centralized medical facilities such as hospitals, medical centers, clinics, and medical/biological labs. PHD may include but are not limited to images (e.g., X-ray images, CT images, MRIs, ultrasound images, mammograms, and vascular images), electrocardiograms, anthropometrics (e.g., weight, height, and 3D body topography), respiratory rate, heart rate, body temperature, and systolic and diastolic blood pressures.

While generation of some PHD, such as CT images and MRIs, currently require complex and expensive equipment that is centrally hosted, generation and collection of other PHD may only require non-invasive technologies that are much more accessible by the general public regardless of location. Portable, affordable, and/or patient-operated health measurement and monitoring devices are now available and can be conveniently distributed in homes, self-service kiosks, as portable biological lab kits, or even as wearables. In the meanwhile, (1) centralized or distributed computing devices/components with capabilities based on machine-learning technologies such as computer vision and other types of artificial intelligence, and (2) computer security technologies for guarding patient and physician identities and data in a global networked environment have emerged.

Distributed health measurement and monitoring devices further enable more frequent or continuous and near-real-time measurements and monitoring of a patient, and may provide comprehensive time-sequence information that may not be available at centralized medical facilities where patient visits are less frequent. Distributed devices may be diverse in form and may generate additional new data. Additional new data may be associated with patient health conditions and thus may provide valuable additional information in helping improve accuracy in health risk assessment, screening, PHCI, and PPRHA.

While the additional new data can theoretically be useful for identifying patient health conditions by physicians, the number of images, the measurements, and image patterns in the data may be too detailed and volumetric to be considered as key factors indicating a health condition by physicians during a patient visit. However, the associations between the measurements and image patterns and health conditions and remedies, may be automatically learned, identified and extracted by computer models trained using complex machine learning algorithms and architectures such as multilayer neural networks. Computer models may be implemented in backend servers specially configured to provide massive parallel data analytics and computational capability for artificial intelligence applications. The patients and the physicians may electronically communicate with backend servers via their terminal and/or mobile devices to form an integral data workflow for data collection, analytics, health risk assessment, PHCI, PPRHA, and monitoring.

This disclosure describes such an automatic, distributed, computer-aided, and intelligent system and platform for health monitoring and data collection/analytics. The system integrates (1) distributed PHD collection servers and devices, (2) centralized or distributed data servers running various intelligent and predictive data analytics engines for health screening, risk assessment, PHCI and PPRHA, (3) specifically designed data structures including quantized health indicator vectors, a quantized PHCI matrix, and patient health condition vectors, (4) portal servers configured to interface with (5) distributed physician terminal devices, and (6) distributed patient terminal devices for receiving health evaluations, delivering interventions and PPRHA items, and for monitoring and tracking patient activities. The various intelligent and predictive engines are configured to recognize, extract and analyze patterns in data from large heterogeneous data sets collected from distributed data collection devices. The architecture of the system and platform disclosed herein further uses a mixed supervised and unsupervised machine learning approach to train various artificial intelligence models with weighted multi-path feedback for retraining the model and improving intelligence of the models (e.g., a PPRHA engine). The system disclosed herein is based on computer technologies and designed to use artificial intelligence tools to solve technical problems in computer-aided health screening, risk assessment, PHCI, and PPRHA.

The intelligent system disclosed herein may be further capable of predicting various types of health conditions and risks for a patient by identifying patterns indicating a health issue from collected data, in addition to particular PHCI and PPRHA items. Risks include, but are not limited to, cardiopulmonary risk, neurological risk, diabetic risk, intestinal permeability risk, intervertebral disc degeneration risk, and other postural risks. Accurate and timely prediction of health risks allows provisioning of preventive measures that may significantly reduce health costs, prevent further illness, and even prevent/delay death. While some of the risk assessment may be traditionally provided in regular medical exams and health screenings, some risks may be unconventional and are more difficult, if not impossible, to assess manually by physicians. For example, risk of falling due to postural imbalance is difficult to assess manually. Yet, a large percentage of deaths in the elderly population are attributed to falling, or indirectly due to complications caused by falling, including hip fractures, cervical fractures, and death due to the decline of posture and balance control. By using the computer-aided system and methodology disclosed below, risk of falling may be predicted intelligently and accurately, using for example, computer-aided analytics of 3D body topography data in the form of 3D body mesh scan and other auxiliary data.

This system thus includes data collection, data analysis, and data storage components that provide more accurate and complete information to assist medical professionals to provide further PHCI, identify health improvement opportunities, and implement interventions to achieve desired outcomes. In different embodiments, this system may be suitable for providing computer-aided rehabilitation, therapeutic PHCI and PPRHA for reducing functional impairments and health complications.

The intelligent system disclosed herein may in particular facilitate unmet health care needs in rural areas by expanding access to care. Health care provisioning in rural areas face various barriers, including but not limited to transportation difficulties, limited supplies, lack of health care quality, lack of health care professionals, social isolation, and financial constraints. Rural residents have higher morbidity and mortality rates compared to their urban counterparts. Distributed PHD collection and remote computer-aided screening, PHCI, and PPRHA described herein may serve as a platform to bypass rural area health care barriers and provide more accessible and effective health services.

The term "PPRHA" is used in this disclosure to broadly refer to any individual or combined preventive or remedial advocacy items prescribed for a particular one or more health conditions. PPRHA items may include but are not limited to prescriptive or nonprescriptive medicine, supplements, self-directed management, at-home care, therapies, medical/biological tests, and referral of medical/clinical facilities or physicians. The term "PPRHA" may be alternatively referred to as patient therapeutic interventions. Likewise, the term "therapeutic" is used herein to broadly refer to prescriptive or nonprescriptive medicine, supplements, self-directed management, at-home care, therapies, medical/biological tests, referrals, and the like based on the patient health conditions.

FIG. 1 shows an example of such a distributed, automatic, and intelligent health monitoring and data analytics system 100. In the embodiment of FIG. 1, system 100 includes distributed PHD collection devices 104 and 106, physician terminal devices 118 operated by physician 120, patient tracking terminal devices 122 operated by patients 124, data repository 112, various data analytics engines including an intelligent PHCI engine 114 and an intelligent PPRHA engine 108, and portal servers 102 for providing the physician terminal devices 118 and patient tracking terminal devices 122 access to the data analytics engines (108 and 114) and data, and for enabling collaboration between the patients 124 and the physicians 120.

As shown in FIG. 1, each component of the system 100 may be located anywhere in the world and some system components, such as the data repository 112 and each of the data analytics engines 108 and 114 and portal servers 102 may further be distributed over multiple geographical locations. Some components of the system 100 may be virtualized and may be implemented in a computer cloud. While only a single instance is illustrated in FIG. 1 for some components of the system 100, the number of instances in an actual implementation is not limited. For example, there may be multiple physician participants 120 and multiple patient participants 124, each being provided with a separate account in the portal servers 102. In addition, each patient 124 or physician 120 may access its account in the portal servers 102 via any number of terminal devices 122 and 118. The physician terminal devices 118 and the patient tracking terminal devices 122 may be fixed or mobile, implemented in forms including but not limited to desktop computers, laptop computers, personal digital assistants, augmented reality devices, mobile phones, and mobile tablets. All components of the system 100 above may be interconnected by communication networks 110. The communication networks 110 may include private and/or public wireless or wireline networks defined by, for example, any known network protocols and/or stacks. The communication networks 110 may implement any security technologies that are currently known or developed in the future for protecting patient and physician privacy during data access and transmission. For example, end-to-end encryption and security protocols that satisfy or exceed, e.g., HIPAA requirements, may be implemented.

The distributed data collection devices 104 and 106 may be installed with various types of sensors. The distributed data collection devices 104 and 106 may be distributed in homes or in a network of self-service kiosks. The distributed data collection devices 104 and 106 may be located in medical centers, hospitals, clinics, and centralized labs. In some embodiments, the distributed data collection devices 104 and 106 may be distributed as wearables, such as watches and bracelets. In other embodiments, the distributed data collection devices 104 and 106 may be configured as an autonomous service kiosk. In some further embodiments, the distributed data collection devices 104 and 106 may be part of and may be integrated with the patient tracking terminal devices 122.

In one particular embodiment, as will be described in more detail below in relation to FIGS. 3 and 4, the distributed data collection devices 104 or 106 may include one or more 3D body scanners. Each of the 3D body scanners 104 or 106 may be capable of generating 3D topography data of a patient body using any suitable scanning technology in the form of 3D body mesh scan. Like other health data, the 3D body topography data may include information that is associated with various health conditions and may be used to facilitate general or specific health screening, health risk assessment, PHCI, and PPRHA. For some particular health conditions, e.g., kyphotic conditions related to postural abnormality, the 3D topography data may constitute a major source of information for PHCI of a particular abnormal postural condition and for corresponding therapeutic PPRHA items (e.g., physical therapy treatments).

Figure 2:
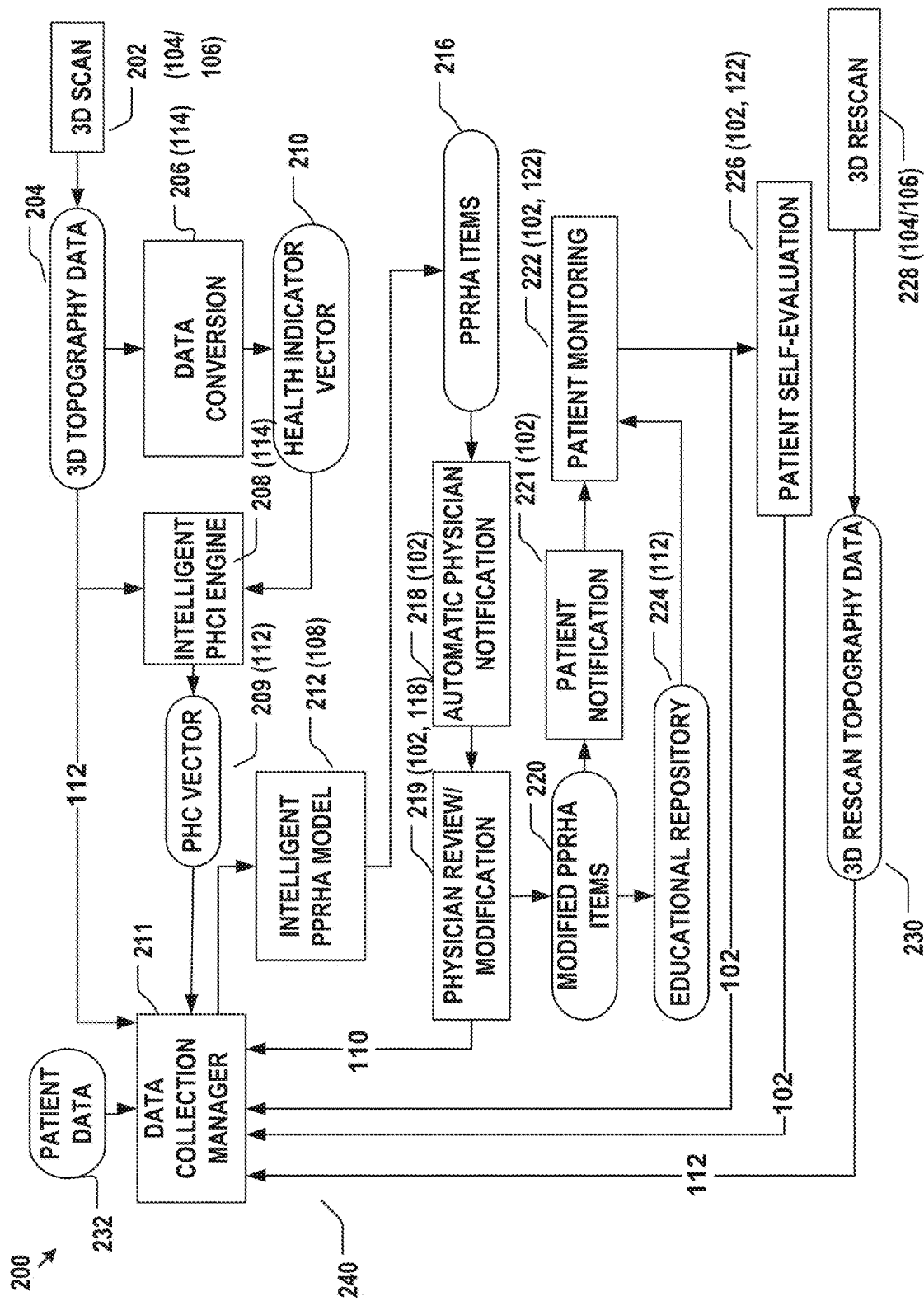
FIG. 2 illustrates an exemplary data workflow for the distributed data processing system of FIG. 1.

FIG. 2 shows an exemplary data workflow system 200 for system 100 of FIG. 1. In FIG. 2, rectangular boxes are used to denote data processing while rounded boxes are used to denote data structures. The arrows indicate directions of data flow. The labels on the arrows indicate main system components of FIG. 1 involved in corresponding data flow. The auxiliary labels in brackets following some of the main labels for various boxes likewise denote the system components in FIG. 1 involved in corresponding processes or used for storing corresponding data. While FIG. 2 uses 3D topographical body scan data as an illustrative example, the underlying principles for data processing, modeling, and analytics in FIG. 2 are broadly applicable to any other type of PHD generated by the distributed data collection devices 104 and 106 of FIG. 1. In FIG. 2, the 3D topography input data may be collected via a 3D scanning process 202 using the distributed 3D body scanner 104 or 106. The 3D topography data 204 may be collected for a particular person for one or more of various predetermined sets of body positions including but not limited to standing, bending, and squatting.

Continuing with FIG. 2, the 3D topography data 204 may be converted in a data conversion process 206 by the intelligent PHCI engine 114 of FIG. 1 to generate a health indicator vector 210 having a vector space including one or more vector components each being an indicator of one aspect of patient health. The health indicator vector 210 may be used by the intelligent predictive PHCI engine 208 (114) in an intelligent PHCI process to generate a patient health condition (PHC) vector 209 corresponding to a PHC vector space including dimensions representing various predetermined health condition (or diseases). Optionally, the full original and unprocessed 3D topography data 204 may also be used as another input to the intelligent PHCI process performed by the intelligent PHCI engine 208 for the generation of the PHC vector 209.

The data workflow 200 may further include a data collection manager 211 which aggregates various data including but not limited to the 3D topography data 204, the PHC vector 209, other patient data 232 (including e.g., patient survey data, patient registration data, and other patient data), and data indicated by arrows 240 (discussed in more detail below). The data collection manager 211 may process data, as will be described in more detail below with respect to FIGS. 17 and 33 and generate input data to the intelligent PPRHA model or engine 212.

The output of the data collection manager 211 may then be input to the intelligent PPRHA model 212 to generate the PPRHA items 216. The automatically generated PPRHA items 216 may be transmitted to the physician terminal device 118 via the portal server 102 and a notification process 218. The PPRHA items 216 may be presented to the physician in a graphical user interface on the physician terminal device 118. The physician may be allowed to review (at 219) the 3D topography data 204 and health indicators of the patient (not shown as an input to process 219 in FIG. 2 for simplicity) and the PPRHA items 216, and provide modification to the PPRHA items 216 (if needed) in a graphical user interface on the physician terminal device 118 to generate modified PPRHA items 220. The modified PPRHA items 220 are then transmitted to the patient tracking terminal device 122 via the portal server 102 and a patient notification process 221. The modified PPRHA items 220 may be presented to the patient in a graphical user interface on the patient tracking terminal device 122. The patient may then implement the modified PPRHA items 220 and the implementation may be monitored by the patient tracking terminal device 122 as shown by process 222. The patient implementation, for example, may be monitored and recorded as logs and stored in the data repository 112.

Patient implementation of the modified PPRHA items 220 may be augmented by educational repository materials 224 extracted from the data repository 112. The educational materials may be selected from an educational library in the data repository 112 based on the modified PPRHA items 220 and the patient-selected educational materials 224 may be presented to the patient via the graphical user interface on the patient tracking terminal device 122 via patient monitoring process 122. Educational materials may include but are not limited to demo videos, text, graphical, simulative, and/or pictorial descriptions for explaining and demonstrating how the modified PPRHA items 220 (e.g., physical therapy exercises) should be implemented.

In some embodiments, the patient may be provided with self-evaluation tools via the graphical user interface on the patient tracking terminal device 122, as shown by process 226. The patient may further be rescanned after implementing a predetermined amount of the modified PPRHA items 220 and/or for a predetermined period of time, or at any time, as shown by 3D rescanning process 228. The rescanned 3D topography data 230 may be recorded in the data repository 112 along with the time of rescan. The rescanned 3D topography data 230 of the patient may further be processed in a manner similar to the original 3D topography data 204 to generate a new health indicator vector. The new health indicator vector may be stored in the data repository 112. As such, the data repository 112 may include a time sequence of health indicator vectors recorded for each patient.

In FIG. 2, the intelligent PPRHA model may optionally be improved by taking into consideration several feedback paths and feedback inputs including but not limited to the physician review and modification of the PPRHA items 219, the monitored log 222 of patient implementation of the modified PPRHA items 220, the patient self-evaluation process 226, and the rescanned 3D topography data 230 and the corresponding health indicator vector (which can be evaluated at different times to form a time sequence). Input feedback to the data collection manager 211 as shown by arrows 240 may be used by the intelligent PPRHA model as additional data for generating the PPRHA items 216 via the intelligent PPRHA model 212, and for facilitating the data collection manager 211 to perform its function in generating an original and updated training dataset for training and retraining the intelligent PPRHA model 212, as described in more detail below with respect to FIG. 17 and FIG. 33.

Figure 3:
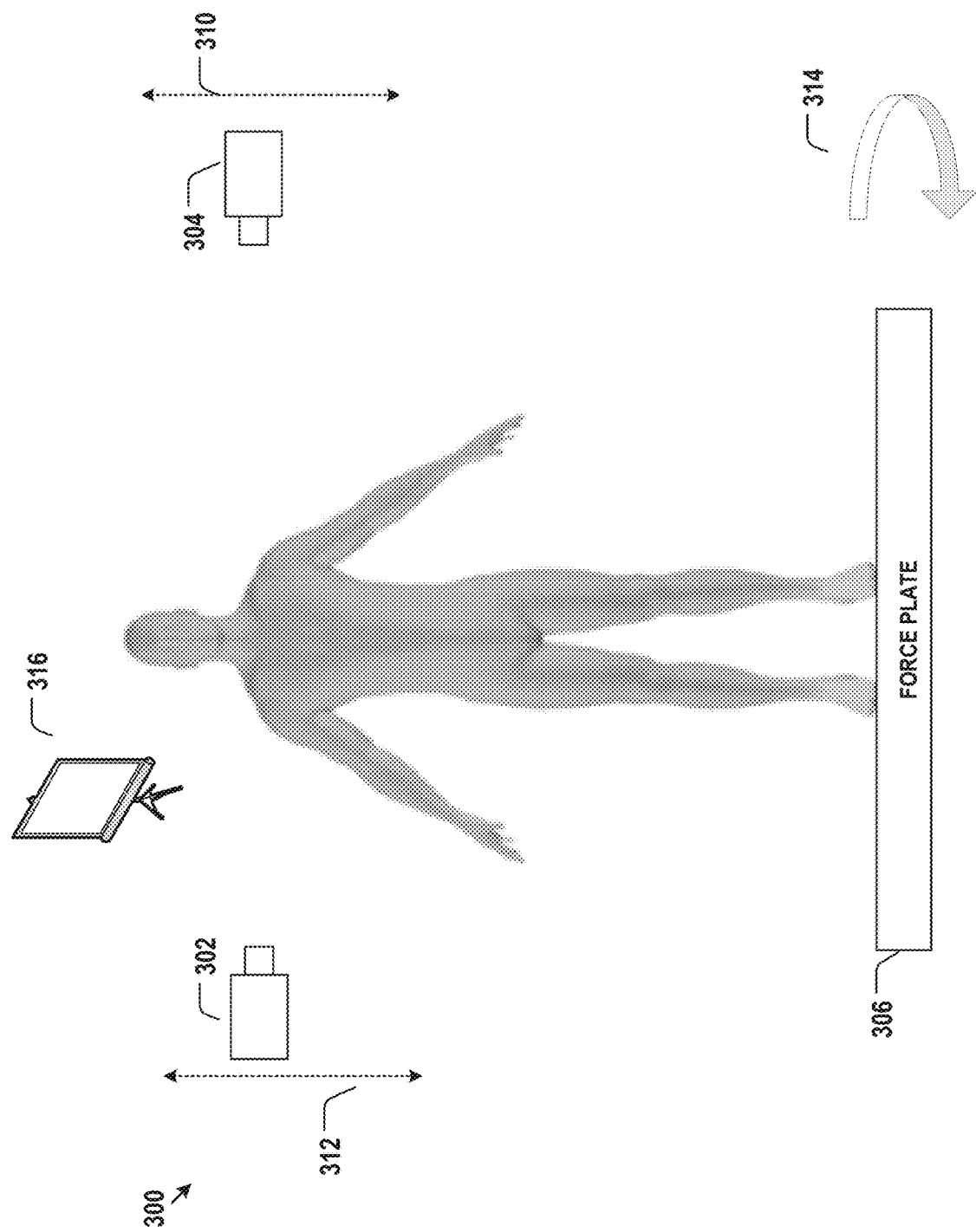
FIG. 3 illustrates an exemplary distributed PHD collection device in the form of a 3D body scanner for producing topographical data in a form of 3D body mesh scan.

FIG. 3 illustrates an example of the distributed data collection devices 104 and 106 in the form of a 3D body scanner 300. The 3D body scanner 300 may include one or more sensors 302/304 and a force plate 306. Sensors 302 and 304 may be implemented as digital cameras or may be based on other optical sensing technologies. Alternatively, sensors 302 and 304 may be implemented as laser scanners using class I laser beams in the infrared optical spectral range. The 3D topography data may be obtained based on, for example, laser ranging and time-of-flight technologies. For another example, sensors 302 and 304 may be based on structured light and optical detection technologies associated with structured light.

The force plate 306 may be configured as a platform for a patient to stand. The force plate 306 may be segmented into independent sensing grids such that both the magnitude and distribution of force or pressure exerted on the force plate 306 may be detected. Sensing grids may determine the static pressure distribution due to patient postural imbalance and dynamic patient functional movement characteristics. Patient postural sway may be captured on the force plate 306 in a single postural snapshot or in a series of continuous or discrete postural snapshots in time. As such, the force plate 306, in addition to the sensors 302 and 304, may provide one or more segmented (or pixelated) pressure or force data that may be used to help determine, for example, the static balancing attributes and the dynamic balancing attributes (or functional movement or sway attributes) for the patient. The force data may additionally be used to establish a reference frame for the 3D body topography data for various predetermined body positions, as described further below.

The sensors 302/304 and the force plate 306 may be configured with motion capability for the collection of body topography data in 3D. For example, sensors 302/304 may be mounted on translation stages such that they may be controlled to move vertically (shown by 310 and 312) or horizontally (not shown in FIG. 3). The force plate 306, for example, may be installed on a rotary stage such that the force plate 306 may be configured to rotate around a predetermined axis, as illustrated by 314. Alternatively, rather than rotating the force plate 306, the sensors 302/304 may be installed on a cylindrical frame configured to rotate around its central axis. The linear motion or rotation of the sensors 302/304 or the force plate may facilitate the collection of the 3D topography data of a patient.

The sensors 302 and 304 may be configured to obtain raw topography data of a patient located on the force plate 306. In some embodiments, the sensors 302 and 304 may be digital cameras and the 3D body scanner 300 may be configured to analyze photographs taken (or images captured) by the sensors 302 and 304 from different positions or angles, and thereafter to extract topographical information using digital object detection and recognition technologies based on multilayer convolutional neural network models. In some other alternative embodiments, sensors 302 and 304 may comprise laser scanners based on optical ranging technology for obtaining body topographical information of the patient.

The components of the 3D body scanner 300 may be configured to obtain a set of topography data and force data for a patient in different postural positions including, but not limited to, standing, bending, and squatting. For each position, the sensors 302/304 and the force plate 306 and their translational/rotational mechanisms may be configured to collect and capture a single snapshot of the patient. The sensors may further be configured to take a series of snapshots of the patient. The 3D body scanner 300 may further include a display screen 316 for displaying menus and showing images or videos demonstrating the various postural positions for the patient when capturing topographical snapshots.

While the description above provides some examples of image sensors 302, 304, and force plate (sensor) 306, other types of sensors may be further included in the 3D body scanner 300 to provide data that can facilitate intelligent and accurate PHCI and PPRHA by the engines/models 208 and 212 of FIG. 2. For example, the 3D body scanner 300 may include cameras that are capable of capturing facial and eye images. As will be described below, facial and eye images may be associated with or indicative of stressors and may further be associated with the postural characteristics of the patient. Such data may be provided to the data collection manager 211 of FIG. 2 to facilitate intelligent PHCI and PPRHA. As another example, thermography sensors may be included with the 3D body scanner 300. Such thermography sensors may be configured to provide detection of temperature distribution of a target patient in addition to topographical data. The temperature distribution information may be indicative of inflammation, increased metabolic activity, and other conditions and may be used in conjunction with the topographical data to facilitate intelligent PHCI and PPRHA by the engines/models 208 and 212 of FIG. 2. Now conversely related to increased heat detection, thermography can detect areas of the body that have decreased temperature that is indicative of decreased blood flow, poor circulation, and other hypovascular disorders. Detecting hypovascular disorders in relation to poor body alignment and posture can give further insights to clinicians regarding the physical health of their patients. For yet another example, sensors based on radio waves, such as electromagnetic waves in the millimeter wavelength range, may be included with the 3D body scanner 300. In embodiments, radio wave sensors may be used to automatically detect pressure changes in a human body without physical contact. The pressure changes may be related to breathing, blood flow, and swelling. For example, a radio wave sensor may detect decreased blood flow in the feet of individuals with poor balance. Such detection will give valuable information relating to abnormal balance conditions. Adding a radio wave sensor thus may further supplement the accuracy of PHCI when used in conjunction with 3D scanning and a force plate sensor. Lastly, red light spectroscopy provides another sensing technique that may be used in conjunction with 3D body scanner 300. Red light spectroscopy can detect the oxygenation in blood flow within a human body.

Figure 4:
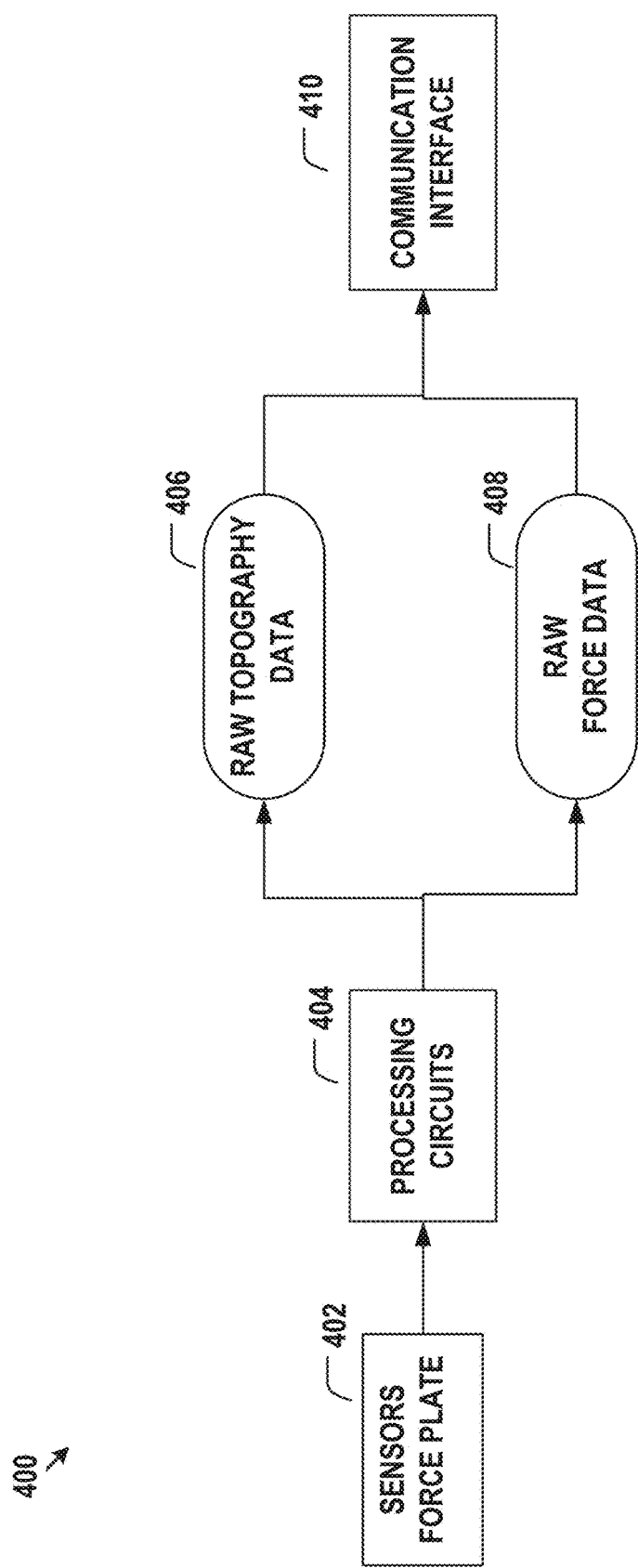
FIG. 4 shows exemplary electronic components of the 3D topographical body scanner of FIG. 3.

The electronic components of the body scanner 300 of FIG. 3, are shown in FIG. 4. The sensors and force plate 402 produce digital signals which may be further processed by the processing circuits 404 to produce raw topography data 406 and raw force data 408. The raw topography data 406 and raw force data 408 may then be communicated to the other components of the system 100 of FIG. 1, via communication interface 410.

Figure 5:
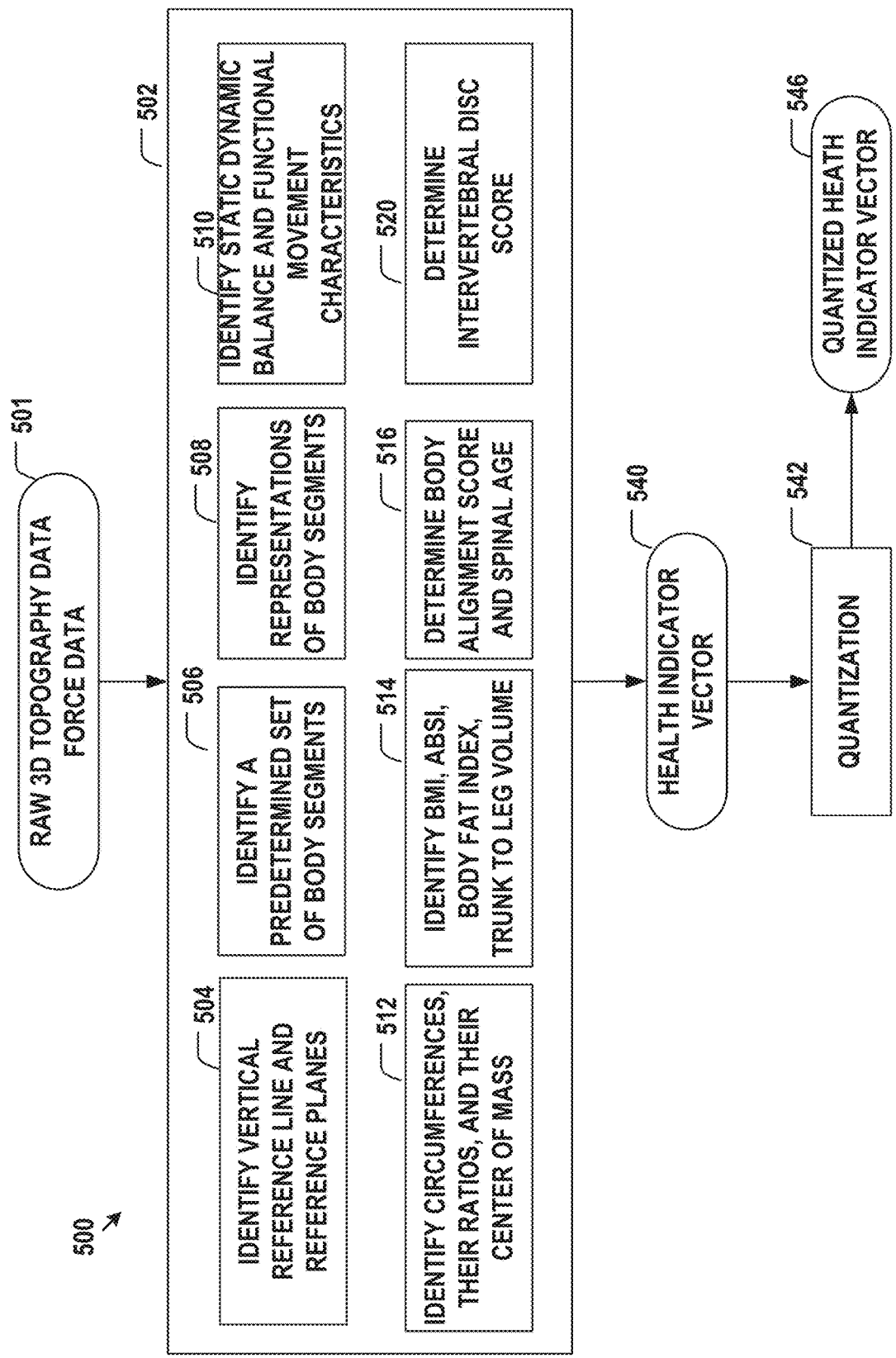
FIG. 5 illustrates data flow for processing and transforming digital information collected from the 3D topographical body scanner of FIGS. 3 and 4 in accordance with the distributed and intelligent data processing system of FIGS. 1 and 2.

The raw 3D topography data 406 and force data 408 may be further processed by the intelligent predictive PHCI engine 114 of FIG. 1 to generate a health indicator vector 210 of FIG. 2. An exemplary data work flow for data processing and analytics is shown in FIG. 5. In this embodiment, the raw topography data and force data 501 may be analyzed by the intelligent predictive PHCI engine 114 using various data analysis processes 502 to generate intermediate data, which are further processed to produce the health indicator vector 540. The health indicator vector 540 may be further quantized using a quantization process 542 to generate a quantized health indicator vector 546. Exemplary components of the health indicator vector 540 and quantized health indicator vector 546 will be disclosed in more detail with respect to FIG. 11 below. The quantization 542 of the health indicator vector 540, may facilitate setting data range limits, simplifying and speeding up data processing following the generation of the quantized health indicator vector 546 in the rest of the PHCI process performed by the intelligent predictive PHCI engine 114 of FIG. 1 and the PPRHA processes performed by the intelligent PPRHA model 212 of FIG. 2. An example for quantization 542 of the health indicator vector 540 will be given in more detail below with respect to FIGS. 15 and 16.

In some embodiments, the data analysis processes 502 may include various exemplary processing components. For example, the data analysis processes 502 may include but are not limited to (1) identifying a vertical reference line and a set of reference planes for normalizing the raw 3D topography data based on the raw 3D topography data and optionally the force data (504); (2) identifying a predetermined set of body landmarks (alternatively referred to as body segments) from the normalized 3D topography data (506); (3) identifying single-point or multi-point representations of body landmarks based on the normalized 3D topography data (508); (4) identifying static and dynamic balance characteristics of the patient based on single body/force plate snapshot or data set of snapshots (510); (5) identifying various circumferences, their ratios, and their centers of mass from the normalized 3D topography data (512); (6) identifying body-mass-index (BMI), a body shape index (ABSI), body fat index or percentage, and trunk-to-leg volume based on the normalized 3D topography data (514); (7) determining body alignment score and effective spinal age based on the normalized 3D topography data (516); and (8) determining an intervertebral disc (IVD) score (520).

Figure 6:
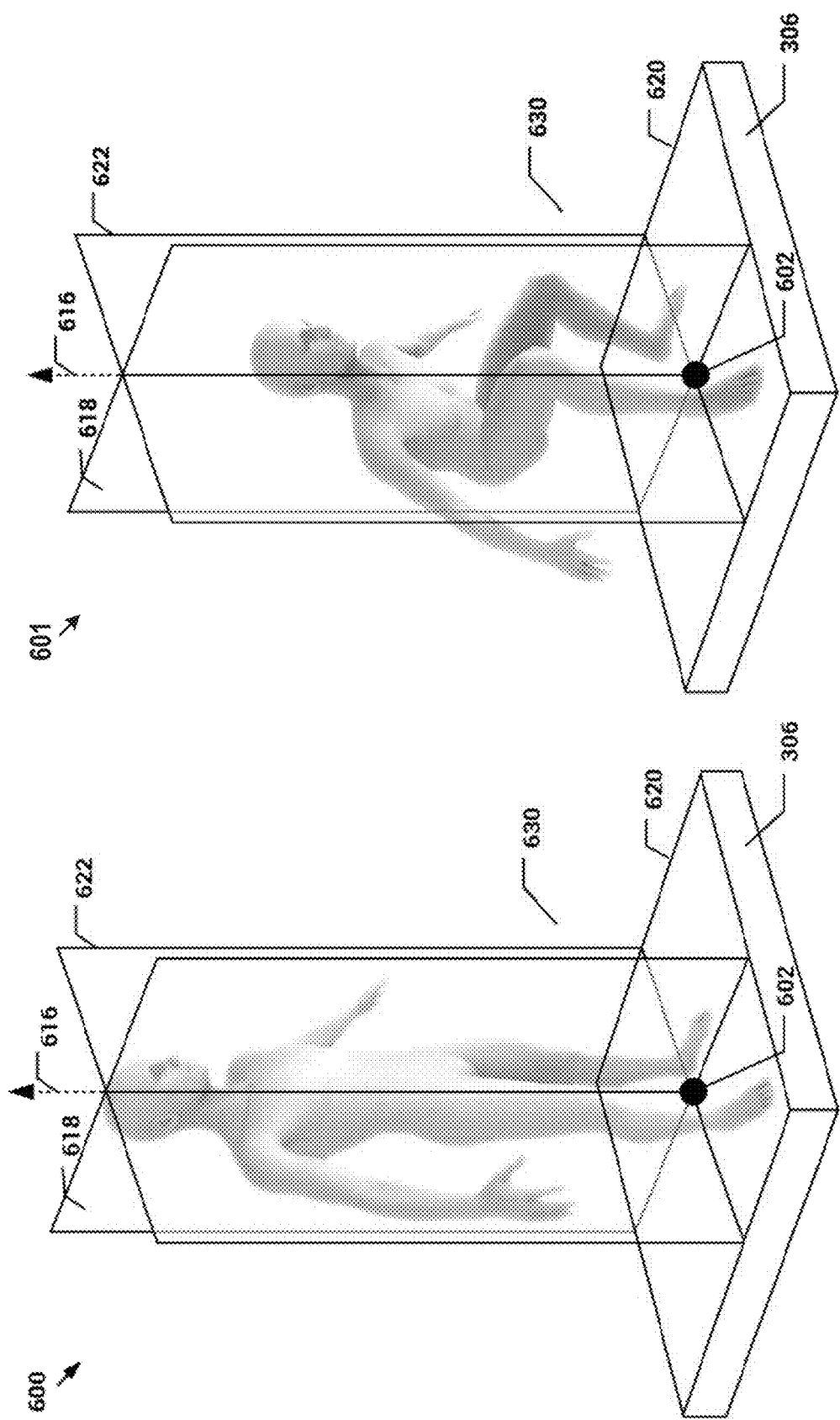
FIG. 6 illustrates an exemplary reference frame for 3D body topography data for two different exemplary body positions.

FIG. 6 shows an exemplary illustrations for the process 504 of identifying the vertical reference line and the set of reference planes based on the raw 3D topography data and/or the force data. The vertical reference line and the set of reference planes may be used to further normalize the raw 3D topography data into orientation normalized for standardized 3D body topography data. The establishment of the reference frame is described in FIG. 6 and below for two exemplary postural positions: standing position (600) and squatting position (601). The underlying principles described here are similar between these exemplary postural positions 600 and 601. The description below for FIG. 6 is based on the standing position (600) but applicable to other postural positions unless otherwise explicitly stated. Corresponding description for data representations in FIGS. 7-10 are also exemplarily given for standing position but applies to other postural positions.

Continuing with FIG. 6 for the standing position 600, and in one embodiment, the heels of the patient may be recognized using computer vision and object recognition models. The center point 602 between the heels may further be determined and may be used to define the vertical reference line 616 of the patient. In some other embodiments, force distribution on the force plate 306, as represented by the force data 408 of FIG. 4, may alternatively be used by process 504 to determine the center point 602 between the heels of the patient. Again, the center point 602 may then be used to determine the vertical reference line 616 of the patient. The vertical reference line 616, for example, may be determined as a line that originates from the center point 602 of the heels and extends in the vertical direction. The vertical reference line 616 in conjunction with the raw 3D body topography data 406 may be used to determine a sagittal plane 618 and a coronal plane 622. The sagittal plane 618, for example, represents a plane intersecting the patient into a left half and a right half. The coronal plane 622, on the other hand, represents a plane perpendicular to the sagittal plane 618 and intersecting the patient into a front half and a back half. The sagittal plane 618 and the coronal planes 622 intersect at the vertical reference line 616. The identification of the sagittal plane 618, for example, may be based on recognition, by computer vision function in process 504, a front-facing direction of the patient according to the raw 3D topography data 406. Such a direction would be normal or perpendicular to the sagittal plane 618. A transverse plane 620 parallel to the ground may be further determined from the raw 3D original topography data 406. The transverse plane 620, for example may encompass the center point 602 of the heels of the patient.

The sagittal plane 618, the coronal plane 622, and the transverse plane 620 further form a body reference frame 630 for the patient in FIG. 6. The original raw 3D body topography data 406 may then be normalized according to the body reference frame 630 to generate the normalized or standard 3D body topography data set. The normalized body topography data, for example may be described using Cartesian coordinates having an origin at the center 602 of heels, and planes 618, 622, and 620 as the Cartesian reference planes.

Figure 7:
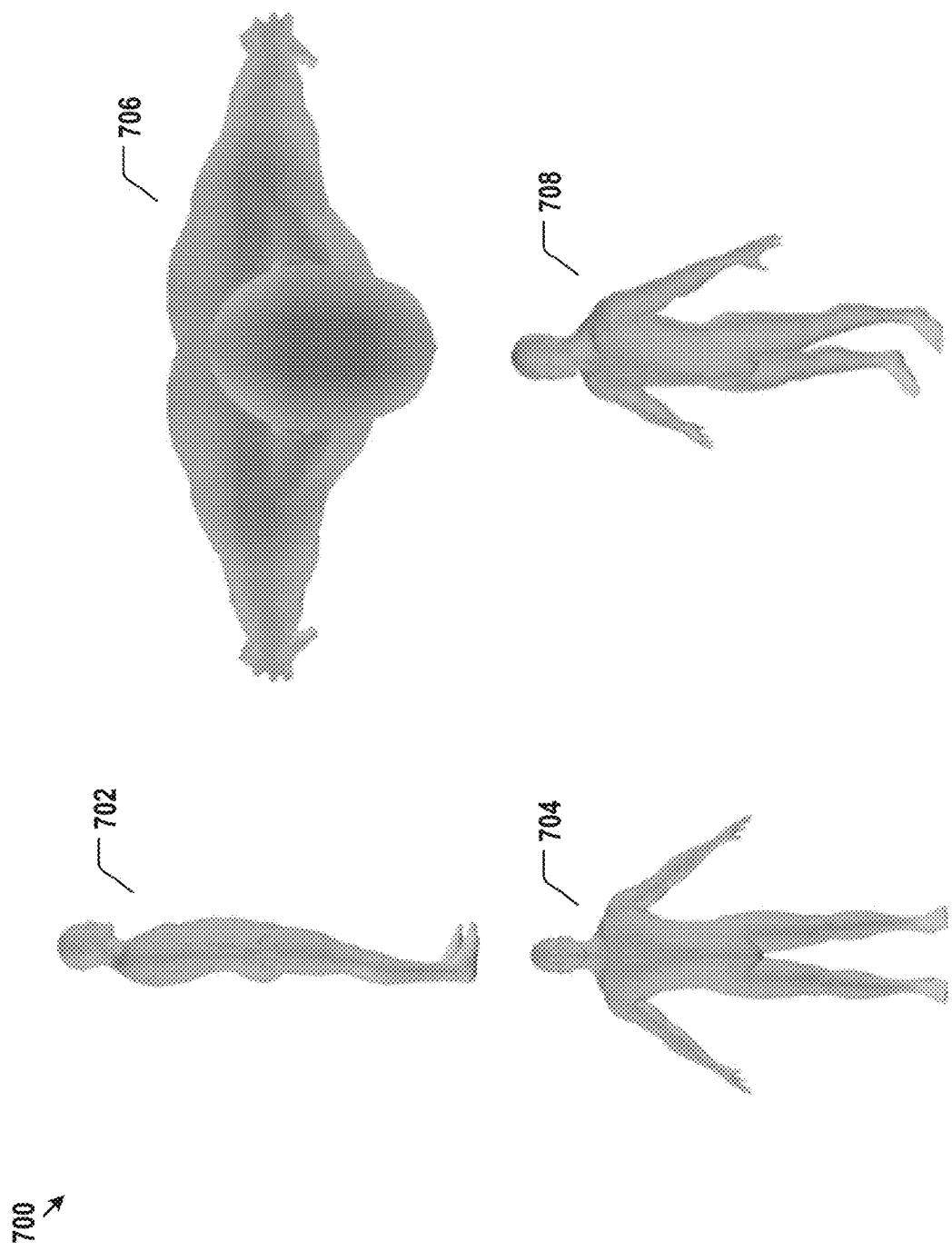
FIG. 7 illustrates 3D body topography data normalized to the reference frame of FIG. 6 and shown in various perspectives and views for one representative body position.

FIG. 7 shows different exemplary views 700 of the normalized 3D body topography data set for the standing position, including side-view 702, front-view 704, and top-view 706. Other views from any predefined angel, e.g., view 708, may also be generated. The views 702, 704, and 706, and 708 may be generated by projecting the normalized 3D body topography data into corresponding projection planes.

Figure 8:
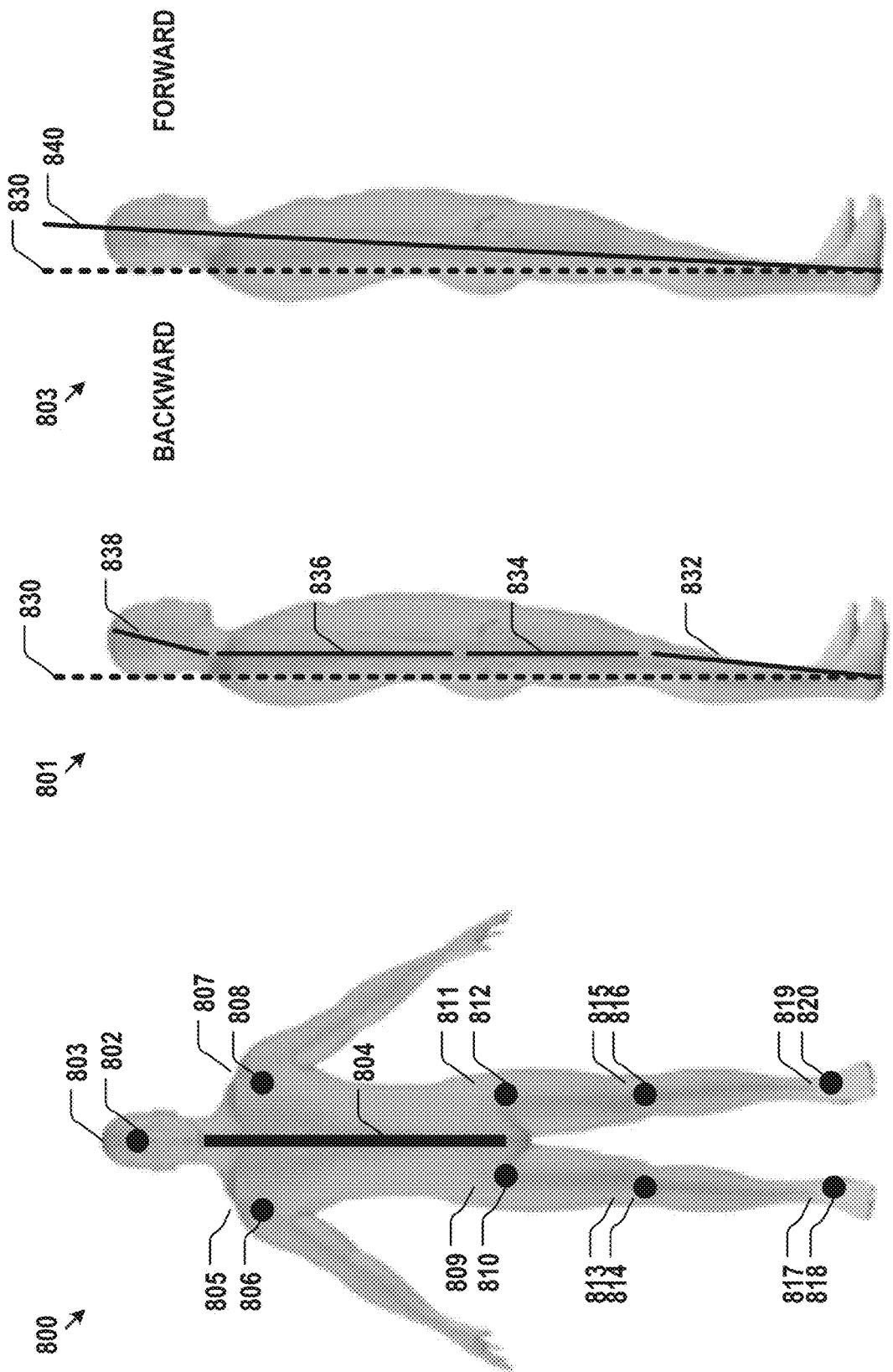
FIG. 8 illustrates identification of body landmarks and their representations, and determination of static and dynamic balance attributes of a patient from the 3D body topography data for one representative body position.

The left panel 800 of FIG. 8 illustrates identification of a predetermined set of body landmarks in accordance with process 506 of FIG. 5 and identification of single-point or multi-point representation of body landmarks in accordance with the process 508 of FIG. 5. The set of body landmarks for example, may include but are not limited to head, 803, shoulders (including right shoulder 805 and left shoulder 807), hips (including right hip 809 and left hip 811), knees (including right knee 813 and right knew 815), and ankles (including right ankle 817 and left ankle 819). In some embodiments, models may output a single-point or multi-point representation for each of the body landmarks in the set of body landmarks. Computer models may be used to recognize from the normalized 3D body topography data portions of the data associated with each of the predetermined body landmarks. Computer models may further output a single-point or multi-point representation for each of body landmarks. For example, single-point representation may be determined for the head, the right shoulder, the left shoulder, the right hip, the left hip, the right knew, the left knew, the right ankle, and the left ankle, as shown by 802, 806, 808, 810, 812, 814, 816, 818, and 820, respectively.

The single-point or multi-point representation above may be derived in the form of Cartesian coordinates in the body reference frame 630 discussed above with respect to FIG. 6. The representation points of body landmarks may be internal to the body surface as represented by the body topography. Likewise, the models above may further output representations of internal body landmarks that are not part of the topography. For example, a multi-point representation 804 forming the spinal line may be determined from the normalized 3D body topography data.

Continuing with FIG. 8, the middle panel 801 illustrates determination of patient static balancing characteristics based on the 3D body topography data and/or the force data using process 510 of FIG. 5. The static balancing characteristics may be used for describing postural imbalance that could pose falling risk. The characteristics are static in that they represent postural imbalance due to static body misalignment. Characteristics may be determined by a single topographic snapshot as shown in 801 and/or corresponding force data. Balancing characteristics may be derived, for example, by analyzing various alignment lines 832, 834, 836, and 838 in conjunction with the body weight distribution along the alignment lines derived from the 3D body topography data in relation to the reference vertical line 830 (616 of FIG. 6). The static balancing characteristics may be further quantified to represent a falling risk for the patient. In other embodiments, the static balancing characteristics may be derived from force data. In particular, the force distribution on the force plate may be analyzed to determine whether the patient is unbalanced in posture. For example, force data showing that the patient weight is more distributed on one heel than the other heel may be an indication that the patient is unbalanced left to right. For another example, force data showing that the patient weight distribution ratio between toes and heals is higher than normal may be an indication that the patient is unbalanced front and back. In yet some other embodiments, the 3D body topography data and force data above may be used in combination to determine the static balancing characteristics for the patient.

The static balancing characteristics above may be obtained from a single snapshot of the 3D topography data and/or force data. Multiple snapshots may be acquired from the patient by the body scanner and analyzed to determine the dynamic balancing characteristics or functional movement characteristics of the patient. Characteristics are dynamic since the snapshots may be taken at different times and used to determine posture instability. Snapshots may be taken as a time sequence. In some embodiments, the snapshots may be taken periodically and/or continuously during a predetermined amount of time. In other embodiments, snapshots may be taken at random times and analyzed statistically to determine the instability of patient posture. Instability in posture may be identified in the form of patient body sway. Patient body sway is shown in the right panel 803 of FIG. 8. Patient body sway may be determined, for example, by detecting deviation of the vertical center body line 840 of the patient from the vertical reference line 830 as a function of time or as a statistical distribution. The vertical center body line 840, for example, may be a line connecting the center of heels and center between the right and left shoulders. Other lines may also be used to represent the vertical center body line 840. The vertical center body line 840 may sway backward, forward, left, and/or right as a function of time, as shown by 830 and 840. The balancing characteristics may be represented by an amount of spread and direction of spread of the vertical center body line 840.

In other embodiments and analogous to the static balancing characteristics above, the dynamic balancing characteristics, e.g., body sway, may alternatively be determined based on a sequence of force data showing variations of force distribution over time for the patient. For example, the pressure distribution detected by the force plate between two feet, between heel and toe of each foot, and within each heel or each toe may vary in time as the patient sways backward, forward, left, or right. The spread of such pressure distribution may be captured by snapshots of force data and used to determine the patient dynamic balancing characteristics, which may include but are not limited to the amount of pressure deviation and direction of deviation.

Like the static balancing characteristics, the dynamic balancing characteristics (or functional movement characteristics) may be quantified and used for representing risk of falling for patient. The dynamic balancing characteristics and static balancing characteristics may be separately analyzed to represent a static risk of falling and a dynamic risk of falling. In some alternative embodiments, the static and dynamic balancing characteristics may be combined to derive an overall risk of falling for the patient.

Figure 9:
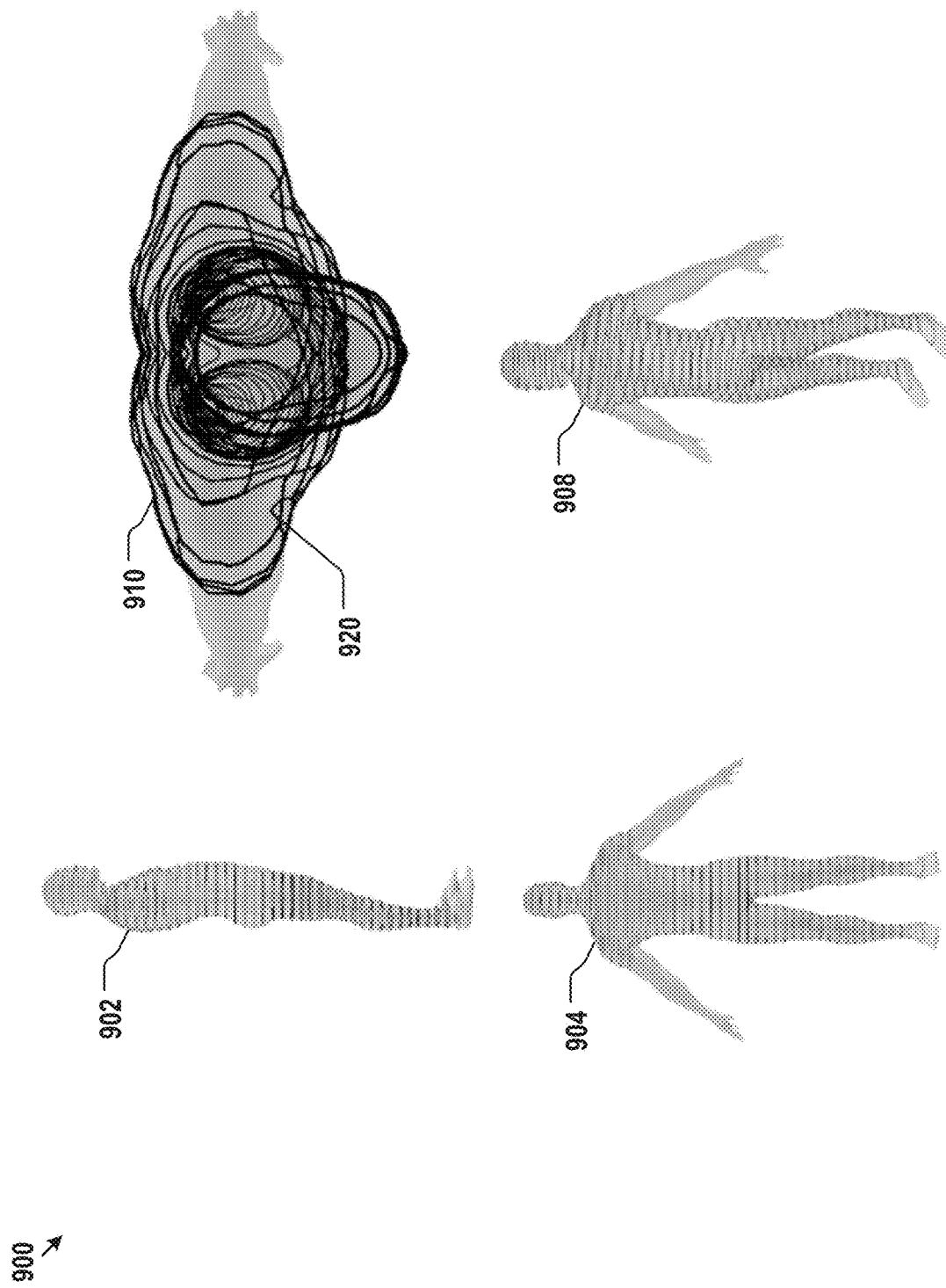
FIG. 9 illustrates computer-aided circumferential measurements based on 3D body topography data for one representative body position.
Figure 10:
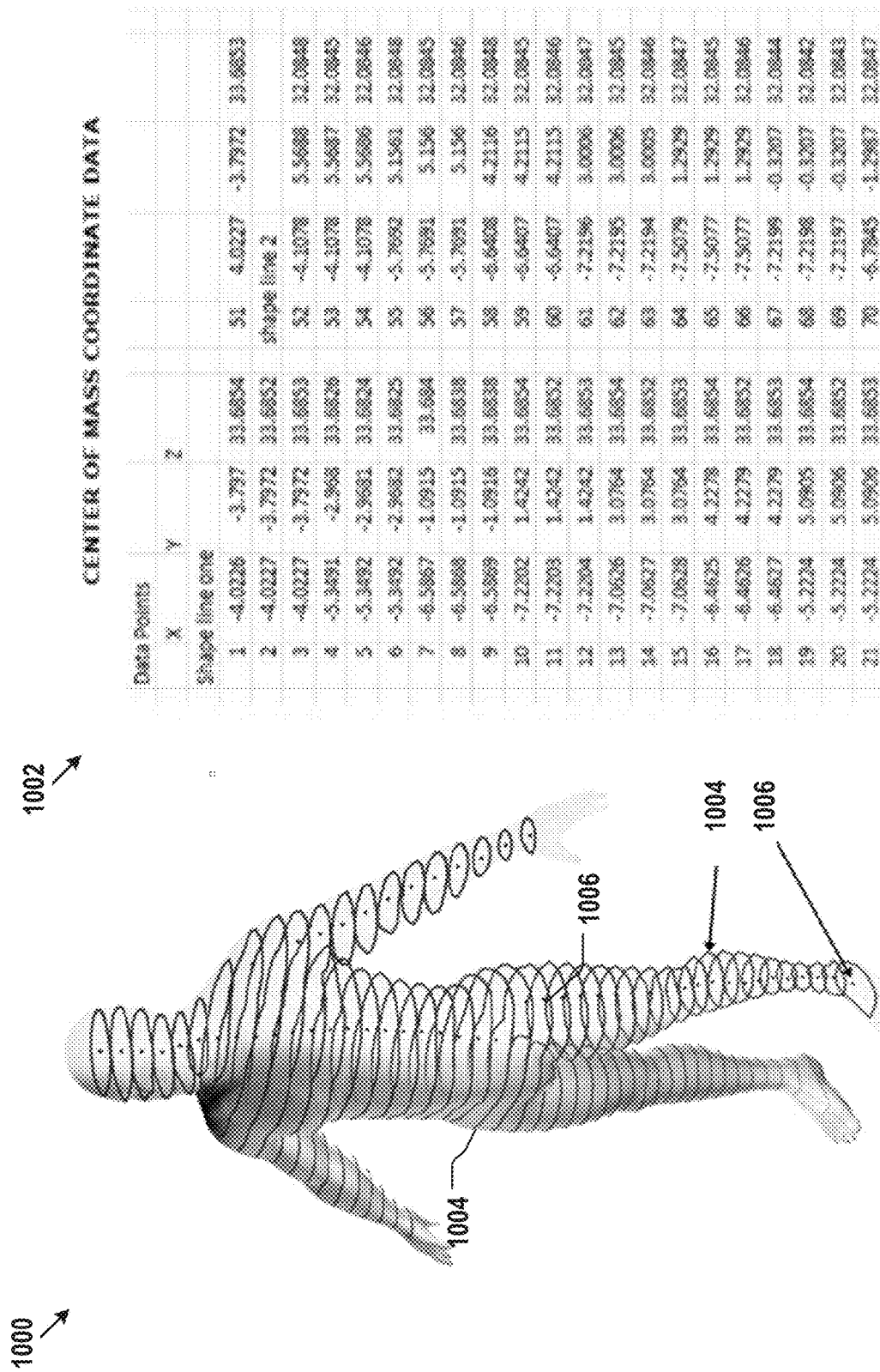
FIG. 10 shows exemplary data describing body circumferences with center of mass derived for one representative body position.

Turning back to FIG. 5 and referring to process 512, FIGS. 9-10 illustrate determination of various body circumferences and circumferential ratios from the normalized 3D body topography data. Ratio between circumferences at different parts of the body may alone or in combination with other parameters provide indication of patient health in various aspects. Circumferences of chest, waist, hips, for example, may be derived from the 3D topography data. The circumferences at different parts of the body may be derived from the scanned topography data with much improved accuracy compared to traditional physical measurements using a tape ruler. For example, traditional measurements of waist circumference using physical measuring tapes may not account for various skin folding and thus may lack measurement accuracy.

FIG. 9, for example, depicts body circumferences 900 in side-view 902, front-view 904, top-view 910 and view 908 along another predetermined angle. Portions 920 of a particular circumference illustrates a skin or surface folding in the patient body that may not be accurately measured using a tape ruler. As shown in FIG. 9, circumferences for head, shoulders, body trunk, and hips may be single circumferences at each vertical position. Circumferences for the arms and legs may include left and right circumferences at each vertical position.

FIG. 10 shows the circumferences 1000 in more detail. For example, particular circumferences, such as 1004, are shown as closed curves. The spreadsheet 1002 further shows the exemplary circumferential coordinates in the body reference frame 630 of FIG. 6 for two particular circumferences (referred to as shapes in 1002 of FIG. 10). FIG. 10 further illustrates determination of center of mass coordinate data for each of the circumferences at various vertical positions, shown as points 1006 in FIG. 10. The centers of mass may be determined by analyzing the shape of each of the circumferences 1004. The centers of mass may form lines as shown by the dots 1006 in 1000 of FIG. 10. The lines, for example, may be further used to determine alignment lines, e.g., lines 832, 834, 836, and 838 of FIG. 8. The alignment lines, as discussed above with respect to FIG. 8, may be used to determine the static and dynamic balancing characteristics of the patient alone or in combination with the force data.

Referring back to FIG. 5, other process such as 514, 516, and 520 in determining various other body parameters, such as BMI, ABSI, body fat percentage, truck to leg volume, body alignment score or quantification, effective spinal age, and IVD score may be further invoked. The processes 514, 516, and 520 are not further shown in additional drawings, but a person with ordinary skill in the art understands the parameters may be derived from normalized 3D body topography data and/or force data.

Figure 11:
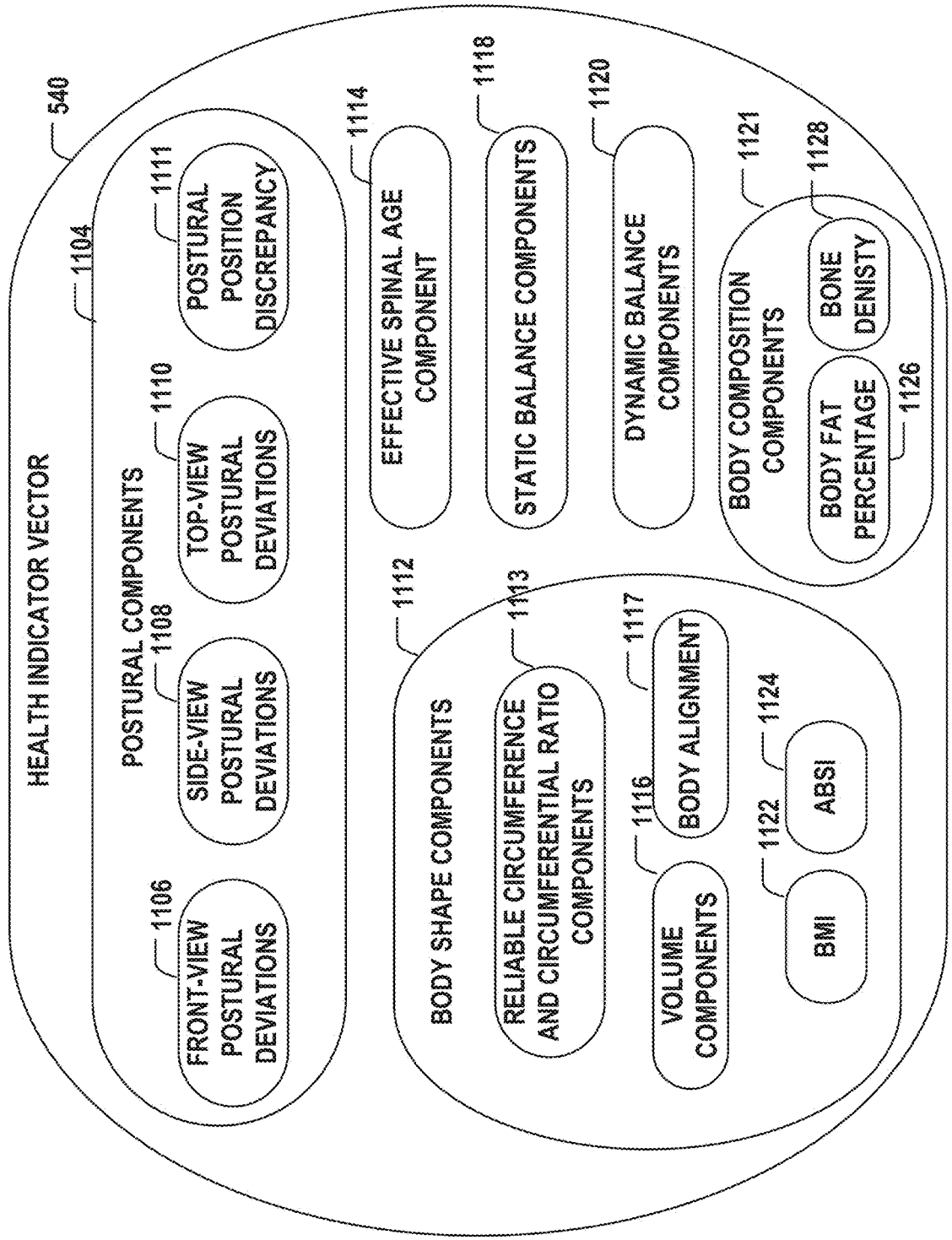
FIG. 11 illustrates an exemplary composition of the health indicator vector shown in the data workflow of FIG. 5.

FIG. 11 illustrates an example of the health indicator vector 540 of FIG. 5. The health indicator vector may include multiple components in a multi-dimensional health indicator vector space. The components may be used as direct or indirect indication of patient health in various aspects. The components may include but are not limited to postural components 1104, effective spinal age component 1114, body shape components 1112, static balance components 1118, dynamic balance components 1120, and body composition components 1121. The postural components 1104 may further include but are not limited to front-view postural deviations 1106, side-view postural deviations 1108, top-view postural deviations 1110, and postural position discrepancy 1111. Postural deviation of each of the predetermined set of body landmarks may be represented by one or more components of the health indicator vector 540. A deviation may be a shift, a tilt, or a rotation of the corresponding body landmark from normal reference values (e.g., zero shift, zero tilt, or zero rotation), as will be disclosed in further detail below with respect to FIG. 12. Postural deviations in different views may be separately represented by deviation components for each of the predefined postural positions described above with respect to FIG. 6 (including but not limited to standing position, bending position, and squatting position). For some patients, severity of postural deviation may differ between different postural positions. For example, a patient may have little postural deviation at standing position but may have significant deviation in other postural positions. Variations of positional postural deviation may be associated with certain postural problems that can be diagnosed and remedied. In some embodiments, a postural positional discrepancy component 1111 may be included as part of the postural components 1104 of the health indicator vector 540. The body shape components 1112, for example, may further include but are not limited to BMI 1122, ABSI 1124, circumferences and circumferential ratio 1113, body volume 1116, and body alignment 1117 components, as discussed above with respect to FIG. 5. The body composition components 1121, for example, may include body fat percentage component 1126 and bone density 1128, which may, for example, be derived from the 3D body scan data.

The various components of the health indicator vector 540 above are merely provided as examples. Other types of components may also be included in the health indicator vector 540. For example, as described above with respect to FIG. 6, the 3D body scanner 300 may include sensors that capture facial or eye images of the patient. Facial and eye images may be analyzed to derive features that are correlated with stressors and other health conditions. The facial and eye features may be associated with postural issues. Identified facial and eye features, when included as one or more components of the health indicator vector 540, may be used by the PHCI engine/model (208 of FIG. 2 above, and 1404 of FIG. 14 below) to associate the data with various health conditions to provide more accurate health condition indication.

Figure 12:
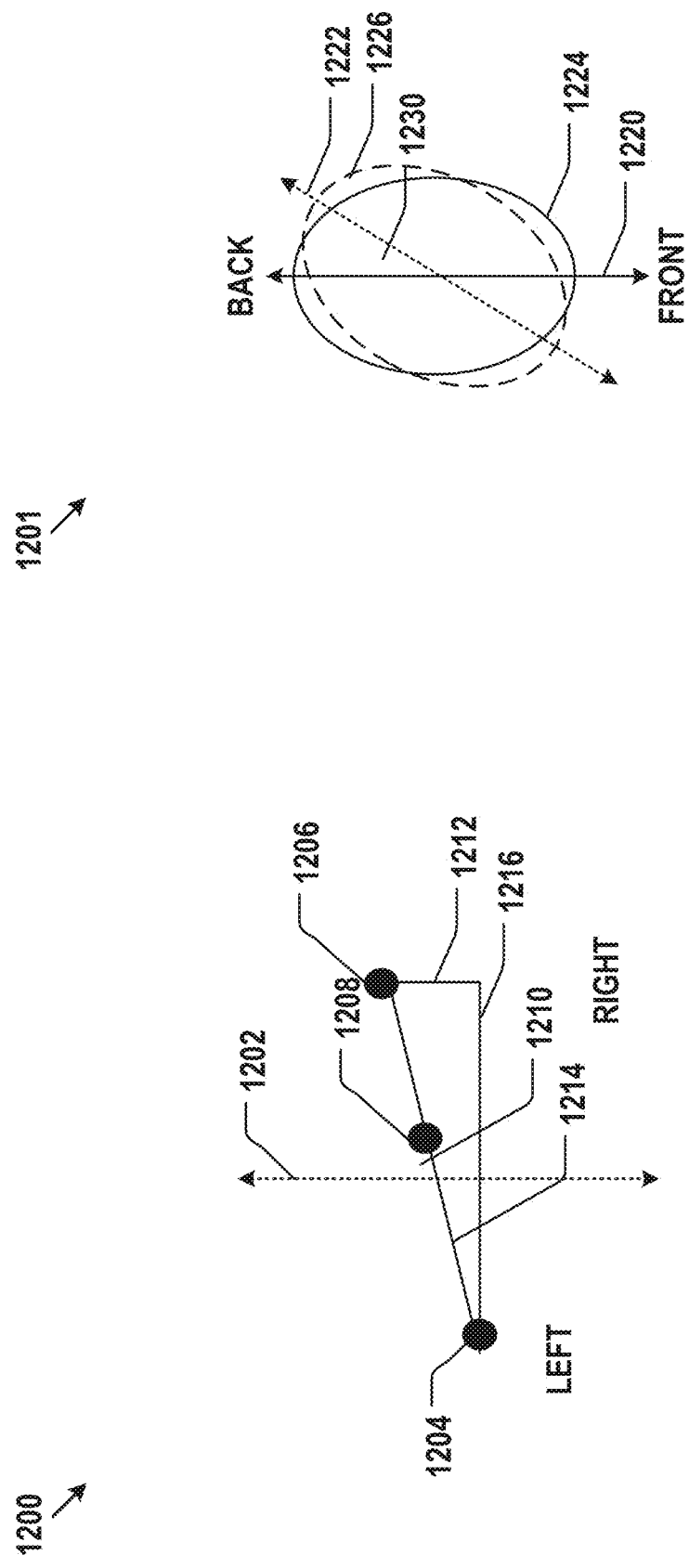
FIG. 12 illustrates exemplary data processing for obtaining postural deviations from 3D body topography data.

FIG. 12 illustrates exemplary embodiments of determining postural deviations of body landmarks (postural components 1104 of FIG. 11) from the 3D body topography data. Postural deviations, for example, may comprise postural shifts, postural tilts, and postural rotations deviating from natural values of body landmarks. Deviations may be ascertained from front-view, side-view, and/or top-view. Postural shifts may be determined as deviation of body landmarks away from the vertical reference line. Postural tilts may be determined as deviation of transverse planes of body landmarks away from the horizontal ground plane. For a body landmark (e.g., shoulder or hip) having left and right parts, corresponding postural tilt may be determined by an angle formed between the ground plane and a line connecting the representation point of the left part and the representation point of the right part of the body landmark. Postural rotation deviation, on the other hand, may be ascertained from the top-view. Postural rotation deviation, for example, may be used to represent abnormal rotation of a body landmark in the horizontal plane around vertical reference axis line.

The left panel 1200 of FIG. 12 illustrates one embodiment for calculating postural tilt and shift deviations. A left representation point 1204 and right representation point 1206 of a body landmark may be determined as disclosed above with respect to FIG. 5. Line 1214 connecting the left representation point 1204 and the right representation point 1206 may be determined. Center point 1208 between the left and right representation points may be identified and its coordinates with respect to the reference frame of FIG. 6 may be determined. The deviation of the center point 1208 from the vertical reference line 1202, as shown by 1210, may be identified as the shift deviation. Furthermore, difference between the left and right representation points 1204 and 1206 along the vertical reference line 1202, as shown by 1212 may be identified. In one embodiment, a ratio between this difference 1212 and the horizontal distance between the left and right representation points (as shown by 1216) may be determined as the tilt deviation. The process for identifying shift deviation and tilt deviation may be applied to body landmarks such as shoulders, hips, and knees.

The right panel 1201 of FIG. 12 illustrates one embodiment for determining postural rotation deviation in top-view. For example, normal body landmark position 1224 in top-view may be represented by axis 1220. The actual position of the body landmark 1226 and its axis 1222 in top view may be identified, again, based on computer vision and object recognition models. A deviation in orientation between the normal axis 1220 (pointing to normal front and back) and the actual axis 1222 may be identified to represent the rotation deviation, as shown by 1230.

The various deviations above, may be sign sensitive, i.e., positive deviation may represent deviation in one direction and negative deviation may represent deviation in an opposite direction. Any other predetermined derivatives of the deviations described above (distances, ratios, or angles) rather than the deviations themselves may alternatively be used to represent the shifts, tilts, and rotations. The derivatives, in turn, may be used as the various postural deviation components 1104 in the health indicator vector 504 of FIG. 11.

Figure 13:
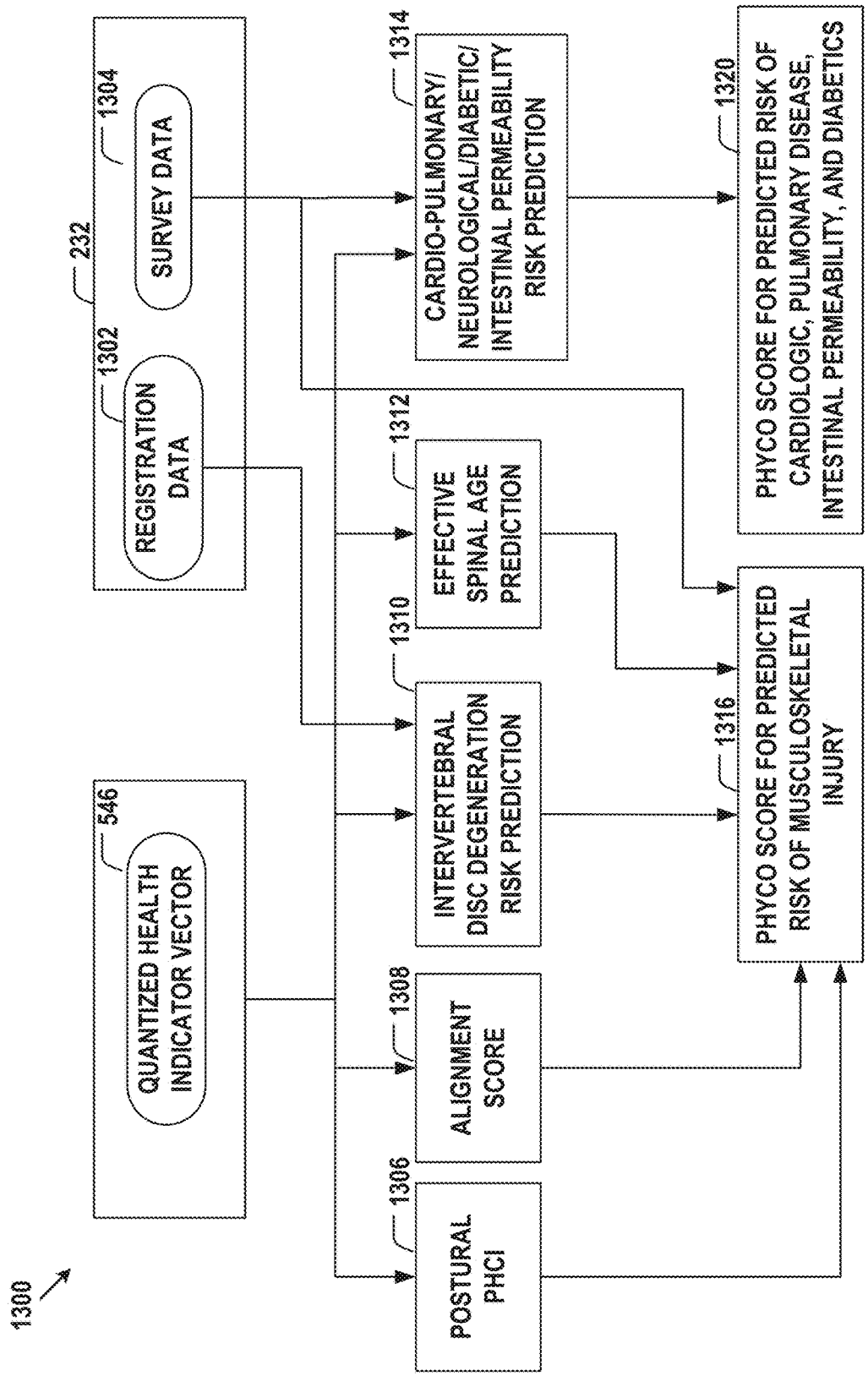
FIG. 13 illustrates an exemplary data processing workflow for obtaining various predictions of health conditions and risks based on the health indicator vector of FIGS. 5 and 11 and other auxiliary data in accordance with the distributed data processing system of FIGS. 1 and 2.

FIG. 13 shows another data work flow 1300 for generation of various health scores for health-screening and assessment using the quantized health indicator vector 546 of FIG. 5 and other auxiliary data. This type of data work flow may be part of the data collection manager of FIG. 2. Auxiliary data, for example, may include but are not limited to patient data 232 of FIG. 2 such as patient registration data and survey data maintained by the portal server 102 of FIG. 1. In one embodiment, the quantized health indicator vector 546 may be used to derive postural PHCI 1306 (as discussed above in FIG. 2 as generated by the PHCI engine), postural and body alignment score 1308, IVD degeneration risk prediction 1310, effective spinal age prediction, 1312, cardio-pulmonary, neurological, diabetic, and intestinal permeability risk prediction 1314. Some postural PHCI, scoring, and risk prediction processes may be augmented by the patient data 232 including, e.g., registration data 1302 and patient survey data 1304 in addition to the quantized health indicator vector 546. For example, some of the risks (such as the IVD degeneration risk, the cardio-pulmonary risk, neurological risk, diabetic risk, and intestinal permeability risk) may be correlated jointly with the quantized health indicator vector 546 and family and individual health history.

Continuing with FIG. 13, various physiological (PHYCO) scores may be further derived for health screening and assessment. For example, a PHYCO score for predicted risk of musculoskeletal injury 1316 may be derived based on postural PHCI 1306, postural and body alignment score 1308, IVD degeneration risk prediction 1310, effective spinal age prediction 1312 and the patient survey data 1304. For another example, a PHYCO score for predicted risk of cardiologic abnormality, pulmonary disease, intestinal permeability (i.e., leaky gut syndrome), and diabetics 1320 may be derived based on corresponding risks 1314.

Figure 14:
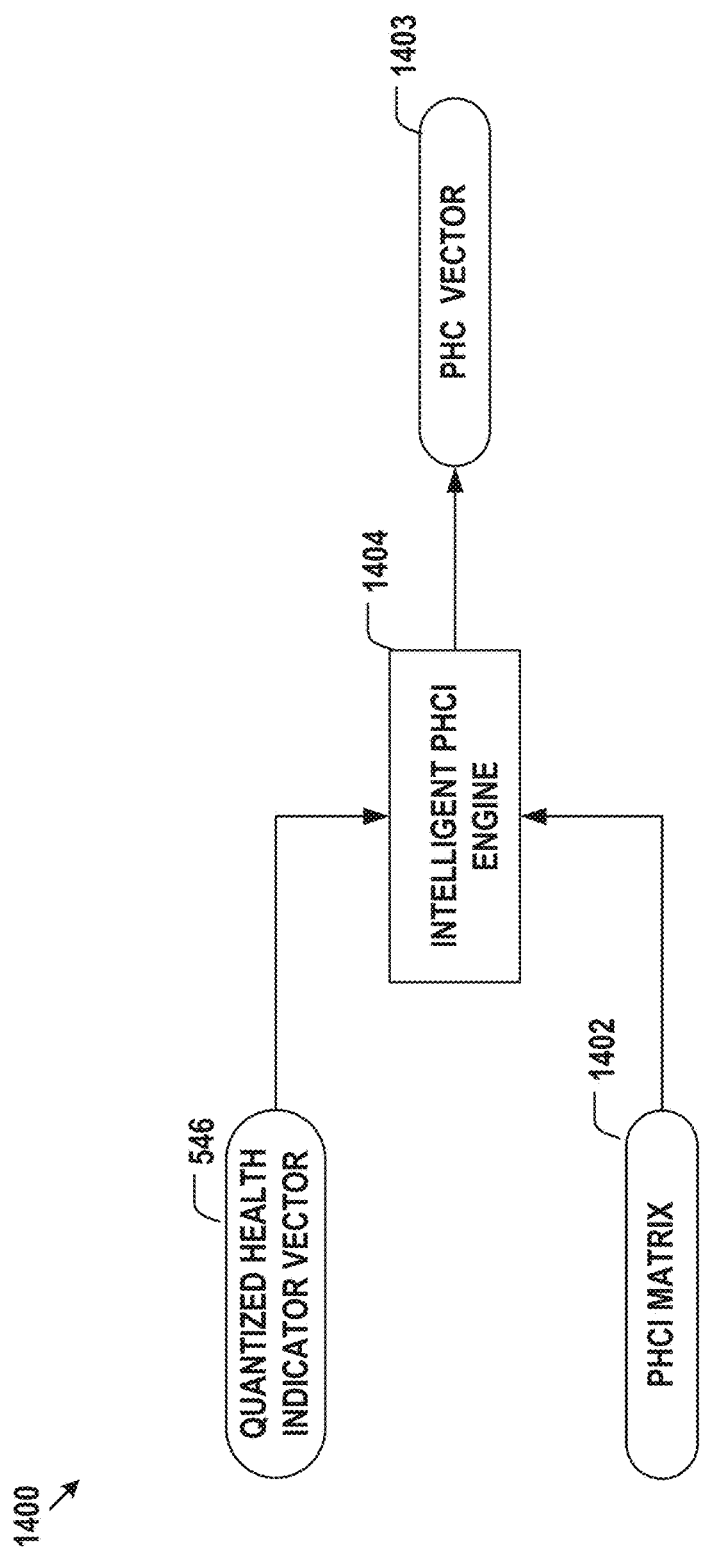
FIG. 14 illustrates an exemplary automatic and intelligent PHCI data workflow in accordance with the distributed data processing system of FIGS. 1, 2 and 13.

FIG. 14 further illustrate an exemplary data workflow 1400 for, e.g., the postural PHCI model to obtain the postural PHCI 1306 of FIG. 13. Those having ordinary skill in the art understand that while the illustration of FIG. 14 is provided in the context of postural abnormality identification, the underlying principles apply equally to computer-aided intelligent identification processes for any other types of health conditions.

As shown in FIG. 14, in one embodiment, the intelligent PHCI engine 1404 may be used to process the quantized health indicator vector 546 and a PHCI matrix 1402 to predict an associated patient health condition (PHC) vector 1403. In some embodiments, the PHCI matrix 1402 may include a first dimension and a second dimension. The first dimension, for example, may coincide with the quantized health indicator vector space. The second dimension may represent a vector space comprised of components that denote a predetermined number of health conditions. Diagnostic conditions may correspond to a subset of patient health condition codes. In some embodiments, various components of the quantized health indicator vector 546 may be weighted by the intelligent PHCI engine 1404 differently. The corresponding weights may be determined during the training process of the intelligent PHCI engine 1404.

Figure 15:
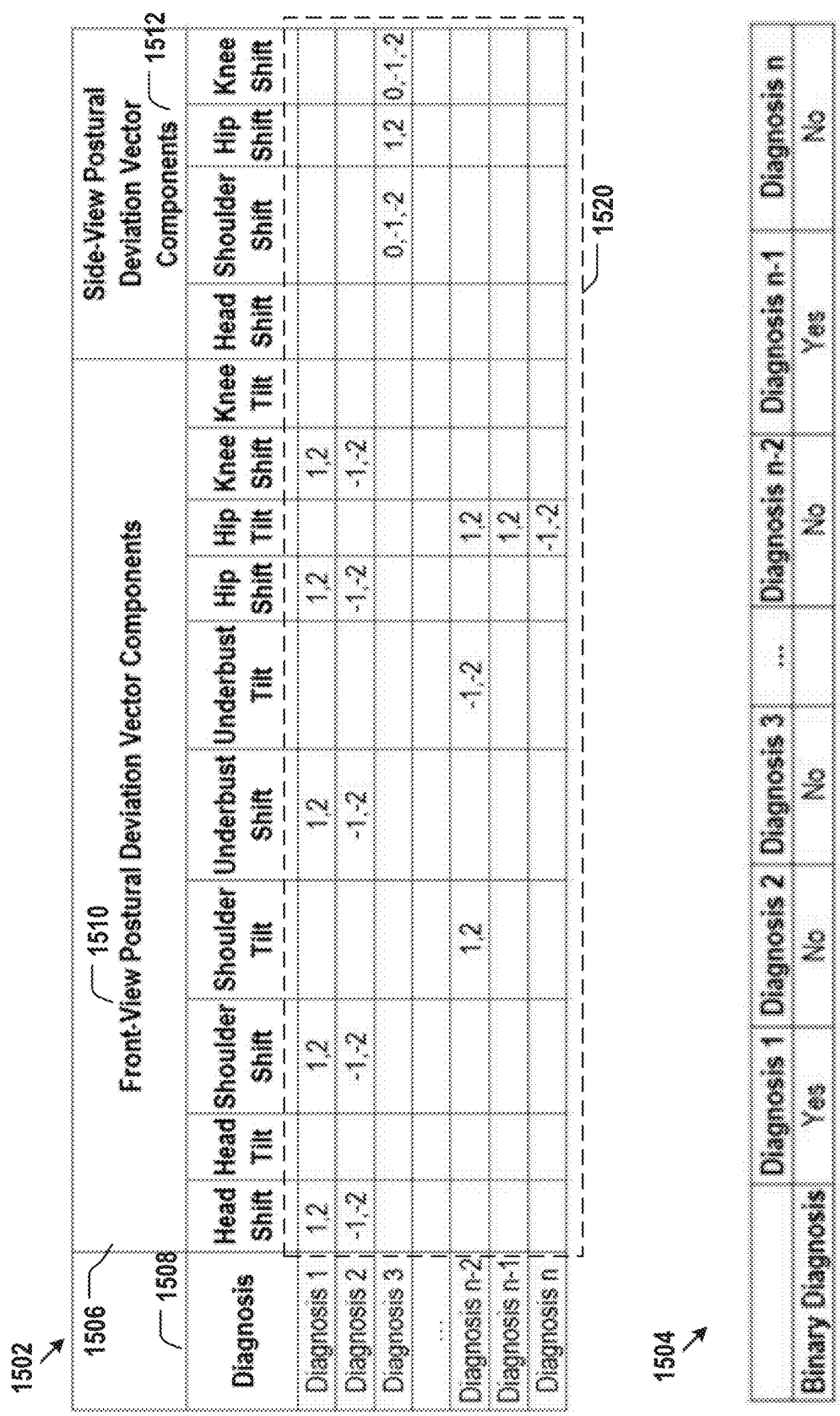
FIG. 15 shows an exemplary PHCI matrix and patient health condition vector in the context of postural abnormality conditions using exemplary postural deviation vector components.

An exemplary postural PHCI matrix is illustrated as 1502 in FIG. 15. The first dimension 1506 of the postural PHCI matrix 1502 may represent various postural deviation components, including but not limited to front-view postural deviation components 1510 and side-view postural deviation components 1512. Other type of postural deviation components, e.g., top-view postural deviation components (not shown in the example of 1502) may be included. Vector components other than postural deviations (not shown) may also be included in the first dimension 1506. The front-view postural deviation components 1510, for example, may include but are not limited to head shift/tilt, shoulder shift/tilt, underbust shift/tilt, hip shift/tilt, and knee shift/tilt. The side-view postural deviation components 1512, for example, may include but are not limited to head shift, should shift, hip shift, and knew shift. The top-view postural deviation components (not shown), for example, may include but are not limited to head, should, underbust, hip, and knee rotations.

The second dimension 1508 of the postural PHCI matrix 1502 in FIG. 15 may include a predetermined set of postural health conditions of interest (shown as "diagnosis 1", "diagnosis 2", . . . , and "diagnosis n"). Health conditions may be selected as a subset of standard postural abnormal conditions used by, e.g., insurance agencies and hospitals. For example, postural conditions may include but are not limited to sway back, scoliosis (right and/or left), trunk shift (left or right), elevated shoulder (left or right), upper cross syndrome, lower cross syndrome, forward shoulder, forward head, leg length discrepancy, and the like. The postural conditions may be associated with standard health diagnosis codes (ICD9). Other health conditions, detectable in some embodiments that include thermal imager sensors to detect body temperature, for example, may be associated with other standard health diagnosis codes (ICD10 for inflammation).

The postural PHCI matrix 1502 may be populated with quantized postural deviation criteria in the first dimension 1506 for each health condition in the second dimension 1508, as shown by the values in various cells in 1520. Within each cell, a postural deviation that must be present for a corresponding postural condition may be listed. Because quantized postural deviation vector components are used, the values list in each cell may be a collection of discrete deviations. As shown in 1520, for some postural conditions, multiple postural deviation components contribute to particular deviation value calculations. The deviation values may all be specified in the corresponding cells. For each postural condition, the relationship between different postural deviation components may be conjunctive or disjunctive, or a mixture of conjunctive and disjunctive relationship. The relationship in 1520 may be default to either conjunctive or disjunctive. The relationship may alternatively be specified using a separate relationship matrix (not shown).

The PHCI matrix 1502 as well as the relationship or relationship matrix discussed above, for example, may be determined using a computer model based on one or more machine-learning algorithms.

Continuing with FIG. 15, an exemplary PHC vector 1504 is illustrated in the context of postural abnormalities. In one embodiment, the PHC vector 1504 may be specified as a binary vector (in other words, each component of the PHC vector comprises a binary value). Specifically, the identification for each postural abnormal condition may be either "Yes" or "No", as indicated in various cells of 1504. In some alternative embodiments, components of the PHC vector 1504 may be comprised of several values or continuous values rather than binary values. A continuous value for a component of the PHC vector 1504 may be used, for example, to represent a probability for a patient to have the corresponding postural abnormality condition. In another embodiment, each component of the PHC vector 1504 may be one of a predetermined set of category values. For example, the predetermined set of category values may be high, medium, and low, representing that the risk level a particular diagnosis component in the PHC vector 1504.

FIG. 16 further illustrates generation of the quantized health indicator vector 546 of FIG. 14, in the exemplary context of quantized health indicator vector 546 indicative of various front-view and side-view postural deviation components. Actual front-view and side-view deviation components for each individual patient (patient "1" to patient "m") derived from the normalized 3D body topography data are shown in measured postural deviation vectors 1600. A quantization table shown in 1602 may be used for quantizing the measured postural deviation components in 1600. The quantization table 1602 may specify, for each postural deviation component, the range of actual deviation value corresponding to each of a predetermined set of quantization levels (−2, −1, 0, 1, and 2 in this particular example, where negative denotes left, and positive donates right). Quantized postural deviation vector 1604 may then be obtained by applying the quantization table 1602 to the measured postural deviation vectors 1600. Each row in 1604 thus represents components of a quantized postural deviation vector (an example of a particular quantized health indicator vector) for a particular patient. Each quantized postural deviation vector may be used as an input quantized health indicator vector 546 in FIG. 14 for obtaining the PHC vector 1403.

Figure 17:
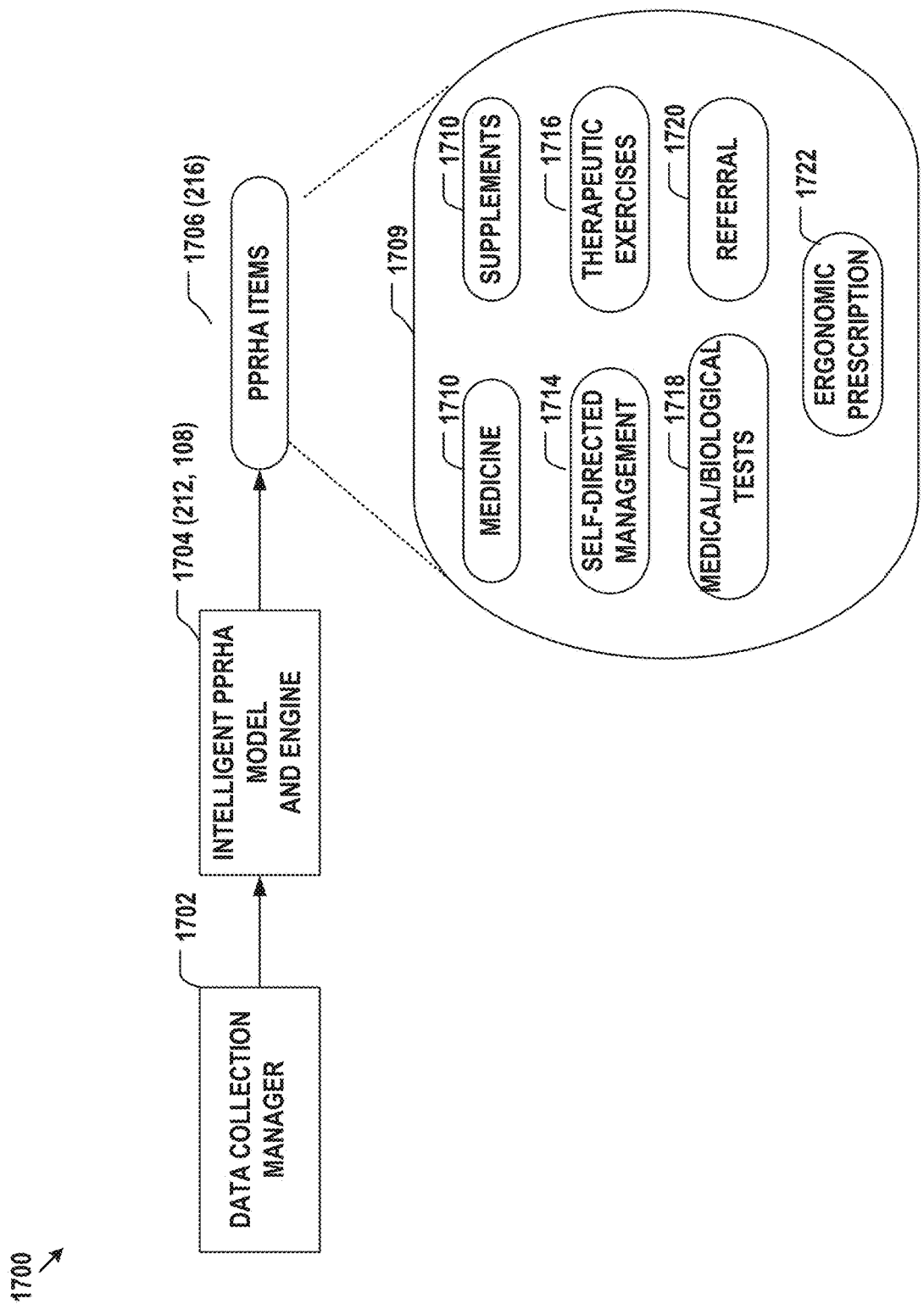
FIG. 17 shows an exemplary data workflow for intelligent PPRHA including a PPRHA model and engine in accordance with the distributed data processing system of FIGS. 1 and 2.

FIG. 17 illustrates an exemplary data work flow 1700 for generating intelligent PPRHA items 1706 using the intelligent PPRHA model and engine 1704 (108 of FIG. 1 and 212 of FIG. 2) based on data collected and processed by the data collection manager 1702 (211 of FIG. 2, including, for example PHC vector 1403 of FIG. 14 and other data). In particular, the output of the data collection manger 1702 may be processed by the intelligent PPRHA model 1704 (or 212 of FIG. 2) residing in the intelligent PPRHA engine 108 of FIG. 1 to generate PPRHA items 1706 (or 216 of FIG. 2).

Figure 33:
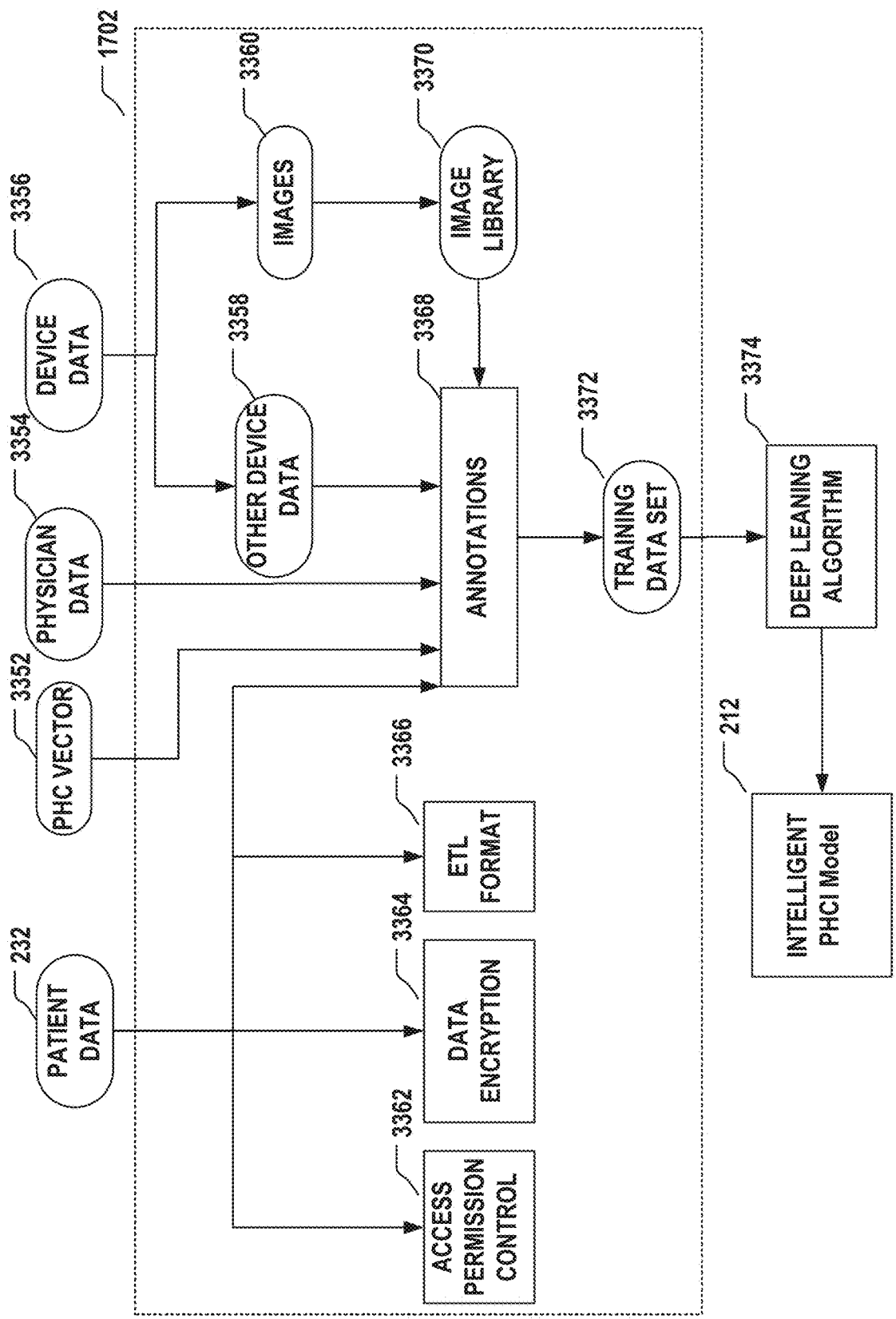
FIG. 33 illustrates an exemplary data workflow for the data collection manager of FIG. 2.

An example data workflow for the data collection manager 1702 is shown in FIG. 33. Input to the data collection manager 1702 may include patient data 232, PHC vector 3352, physician data 3354, and device data 3356 (such as 3D body topography data). The data collection manager 1702, for example, may be configured to handle a variety of tasks. For example, the data collection manager 1702 may handle data access permission control 3362, data encryption 3364, and Extraction, Translation and Loading (ETL) of data 3366. The data collection manager 1702 uses extraction to read data in from multiple data sources, translation to convert the disparate data into one type of format and load to save the formatted data in the system for future retrieval. Device data 3356 may include images 3360 (such as 3D body topography images) and other device data 3358. As shown in FIG. 33, the data collection manager 1702 may be further configured for generating and updating a dataset for training 3372 and retraining the intelligent PHCI model or any other intelligent models discussed above. As such, the data collection manager 1702 may include an annotation function 3368, which analyzes various input data, such as PHC vector 3352, physician data 3354, device data 3356 (including images 3360 via an image library 3370), and performs labeling in the training dataset 3372. The training dataset 3372 may be used by a deep learning algorithm 3374 to train the intelligent PHCI Model 212 (or other intelligent models discussed above).

The Deep Learning algorithm 3374 may be used to automate pattern recognition and identification in the data collected by the data collector manager 1702, including images 3360 and other device data 3358. The PHCI model 212 may comprise a multi-layer feed forward convolutional neural network iteratively trained based on a hybrid of supervised and unsupervised learning. For example, the PHCI model 212 may be trained initially using expert labeled or annotated input data saved in the image library 3370 to recognize patterns in the expert labeled input data. The initial supervised learning may include (1) developing a pattern class, a set of patterns with common properties and attributes that are of comparative interest, (2) presenting prototype or train input to system, (3) preprocessing data into separate segments (characters, image parts, etc.), (4) extracting key features of data to expedite pattern recognition, (5) classifying the categories the features belonging to a given pattern, (6) context processing the data and extracting relevant information pertaining to the data and its environment to increase recognition accuracy.

As collection of data grows while the PHCI model 212 is being used, unsupervised learning may continuously take place. In particular, in order to perform unsupervised classification, where the pattern is not known, the system will determine an unknown class by creating it. Additionally, the system will recognize which class to choose when pattern classes overlap with the primary goal being to choose a class while minimizing the error of incorrect categorization.

After the input is compared to all stored examples, a distance matching score is calculated. The example with the highest matching score is chosen as the cluster the input will belong to using lateral inhibition of nodes. The Hamming distance between the exemplar and the input is then inserted into a vigilance ratio equation. If the ratio exceeds a vigilance threshold, the input is considered to be similar enough to the exemplar, and that exemplar is updated by adjusting the weight connections between it and the input. If the ratio is less than the vigilance threshold for all of the exemplars (the comparison layer), the input (the recognition layer) is considered unique enough to be its own new cluster.

Figure 34:
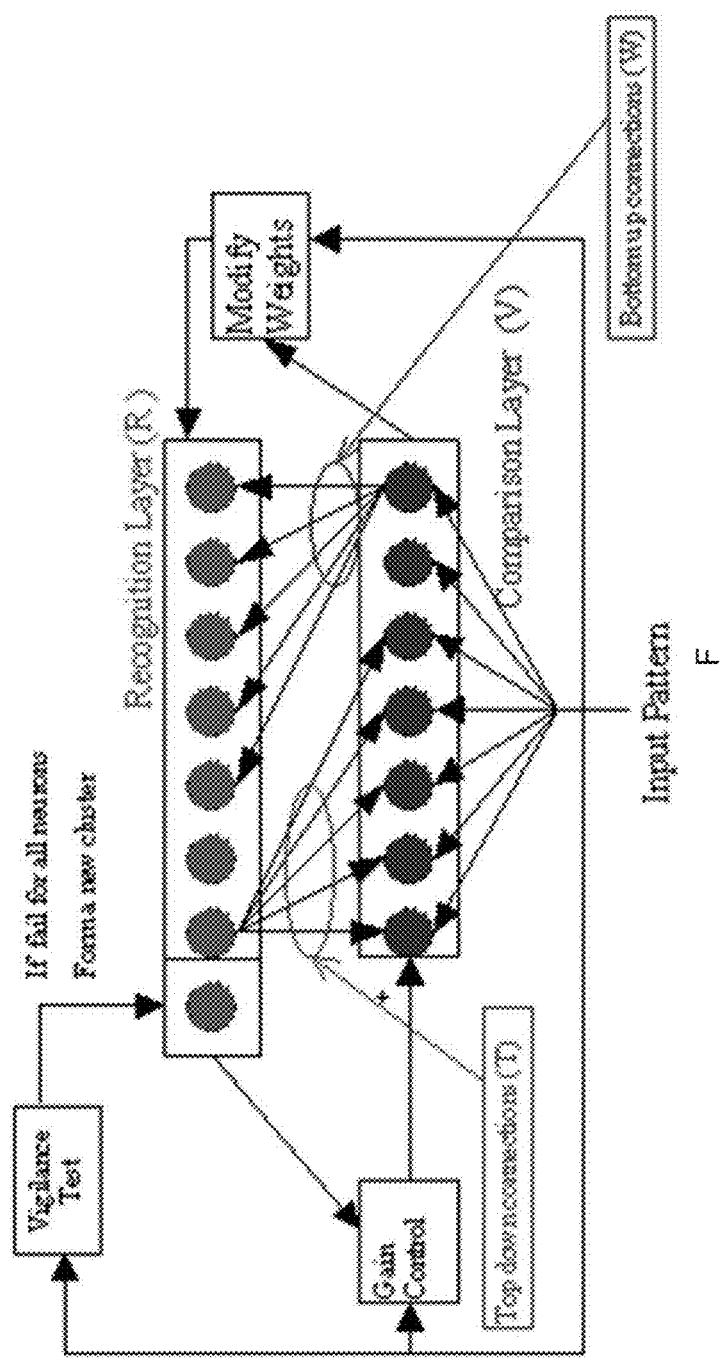
FIG. 34 illustrates an exemplary embodiment of a deep learning model.

A simplified diagram of an architecture of an initial Deep Learning network 3400 is shown in FIG. 34 including two neural layers (comparison layer V and recognition layer R). Neurons of the network 3400 is shown as circles in FIG. 34. Mathematically, the signal of a neuron which fires is 1, while a neuron which does not fire is 0. The output of the recognition layer neuron, j, is:

$V_{out}=1$ if $I_{in}>I_t$ $V_{out}=0$ if $I_{in}<I_t$ where $I_{in}=\Sigma_{i=1}^M W_{ij} V_j$, $V_j$ is the input signal to neuron j, the same as the output of the $i_{th}$ comparison layer neuron (V), and $W_{ij}$ is the weight of the connection between the $i^{th}$ neuron in layer 1 and the $j^{th}$ neuron in layer 2. The value of each ij connection and weight is computed randomly and asynchronously, or in other words in parallel, as a parallel processor. Variables with subscript i vary from 1 to m, while variables with subscript j vary from 1 to n.

The network 3400 uses feedback between the comparison layer V and recognition layer R until the output of the first layer after feedback from the second layer is equivalent to the original pattern which was used as input to the first layer. The degree of this equivalence is dependent on the predetermined vigilance threshold parameter.

Each neuron j in the recognition layer R has a weight vector $W_j$ associated with it. This vector represents a stored pattern for a category of input patterns. Each neuron j receives as input, the output of the comparison layer (vector V) via the weight vector $W_j$. $V_{out}$ is a step function and will always have a binary value of 1 or 0. Each neuron j in the comparison layer V will receive input pattern X, a gain signal (which is 0 or 1), and a feedback signal from the recognition layer R (as a weighted sum of the recognition layer outputs. The feedback $F_i$ through binary weights $T_{ji}$ is:

$$F_i = \sum_{j=i}^{N} T_{ji} R_j$$

with the comparison layer V having 1 to M neurons and the recognition layer R having 1 to N neurons. The vector $R_j$ is the output of the $j^{th}$ recognition layer neuron. $T_j$ is the weight vector from the recognition layer R neuron j.

Learning and pattern recognition take place with new "learned" categories of patterns. The tool proceeds with stability using self-regulating control for competitive learning. Patterns are viewed as points within an N-dimensional space. The patterns are clustered based on proximity of one pattern space to another. A pattern belongs to the class it is closest to. In some cases the clusters will overlap. For our example, a patient may have more than one disease, or some symptoms from several diseases suggesting a new disease.

Competitive learning takes place by creating a standard to make possible a winner-take-all occurrence. Within a layer, the single node with the largest value for the set criterion is declared the winner. If two or more neurons within a layer meet the same largest value, an arbitrary rule, such as select the first, will choose the winner. The input is processed with feedback between its two layers until the original input pattern for the first layer matches the output in the first layer after feedback from the second layer. The degree that the input of the first layer matches the output of the first layer is called the vigilance parameter. This predetermined constant is an input variable, for the neural network.

Back to FIG. 17, the intelligent PPRHA model and engine 1704 forms the core for the generation of PPRHA items. As discussed above, the PPRHA model may be trained to extract explicit as well as hidden features and correlations into a set of model parameters.

The output PPRHA items 1706 may be a combination of subset of PPRHA items among a predetermined full set of PPRHA items 1709. PPRHA items may include but are not limited to medicine 1710, supplements 1712, self-directed management 1714, therapeutic exercises 1716, medical/biological tests 1718, referral 1720, and ergonomic prescription 1722. A referral 1720, for example, may include referral to general types of medical facilities or clinics (such as therapeutic facilities, orthopedic clinics, emergency rooms, and chiropractic facilities). A referral 1720 may alternatively or additionally include specific physicians or practitioners. PPRHA items are not meant to be mutually exclusive. For example, therapeutic exercises 1716 (such as physical therapies) may be self-directed. In the context of PPRHA for abnormal postural conditions, the full set of PPRHA items 1709 may include various types of physical therapeutic exercises, and a subset of exercises may be intelligently selected by the PPRHA model and engine 1704 for a particular input PHC vector. The intelligent PPRHA may include implementation quantity and frequency for each of the prescribed item.

For example, the set of physical therapeutic exercises may include but are limited to static hook lying, mermaid, double leg kneeling twist, sacral rolling, standing hip shift, catcamel, prone dolphin, seated roll down, floor diamond, rotational kneeling, sitting scapular roll, prone chin tuck, floor angel, wall angel, pectoral muscle stretch, bridge, neck sit up, and plank. In some embodiments, the set of exercises may include several hundred different types.

In some other embodiments, the PPRHA items 1706 for abnormal postural conditions may be wholly or partially in the form of ergonomic recommendations 1722. In particular, the intelligent PPRHA model may be trained to output an ergonomic information that facilitates improvement of postural conditions. Such ergonomic information may be used for designing customized apparels, beddings (e.g., including mattresses, sleeping pads, and pillows), braces, support devices, chairs, desks, and/or computing devices/accessories (such as computer keyboard and pointing devices).

The PPRHA model and engine 1704 may further provide prognosis through detailed analysis not performed by a physician and thus may provide more accurate and new, personalized PPRHA. For example, customized rather than standard PPRHA (e.g., number of physical therapy sections) may be provided to each patient based on data analyzed by the intelligent PPRHA model and engine 1704 for the particular patient. For another example, a standard physician prescription (as a form of PPRHA) for body pain after minimal screening may be an expensive magnetic resonance imaging (MRI) procedure. In addition to costliness, the MRI imaging system's strong magnetic field can heat up embedded metal and disrupt the activities of medical devices, a concern for patients with metal, such as shrapnel, embedded in their bodies, or an implanted medical device, such as an older pacemaker or a cochlear implant. Alternatively, the intelligent PPRHA model and engine 1704 may analyze patient data and images to determine an MRI is unnecessary for this patient visit. Further, because the PHD can be collected again at any time (e.g., 3D topography data can be rescanned at any time) and the PPRHA model and engine 1704 evaluates the current PHC vector (included in 1702) with respect to historical PHC vectors, the PPRHA engine 1704 may reevaluate whether and when an MRI procedure should occur, avoiding unnecessary PPRHA testing. In some embodiments, the intelligent PPRHA engine 1704 will include a triage/decision support system to enable at-risk patients to be matched to the appropriate provider type. The intelligent PPRHA system determines referrals intelligently by selecting the provider type for the patient and health condition with the highest probability of optimal outcome. For example, the system may recommend a referral to a primary care doctor vs. physical therapist vs. emergency room visit vs. orthopedic surgeon vs. pain management doctor for a patient based on the health conditions and patient needs from the PPHRA. The medical costs and patient outcomes vary tremendously between visit types, and outcomes are dependent based on the individual characteristics as determined by the health indicator vector and auxiliary data.

Intelligent referrals may be further enhanced through Outcome Registries. Outcome Registries use Patient Recorded Outcome Measurement (PROM)/Medially Validated Questionnaires (MVQ) to assess improvements in the health of a patient before and after medical treatment. The main purpose of outcome reporting is allow insurers to evaluate appropriate payment based on the value of care. The outcome data can be additionally used to rate the quality of providers, from which a directory of trusted providers can be created. Quality providers may be personalized to specific patient attributes/needs determined by the scanned image data and auxiliary data. For example, some physical therapists may attain an excellent rating for knee injury treatment, but a poor rating for spine injury rehabilitation. The PROMs/MVQs may be collected and integrated into the machine learning system via the patient portal, or via other existing outcome registry databases.

Figure 18:
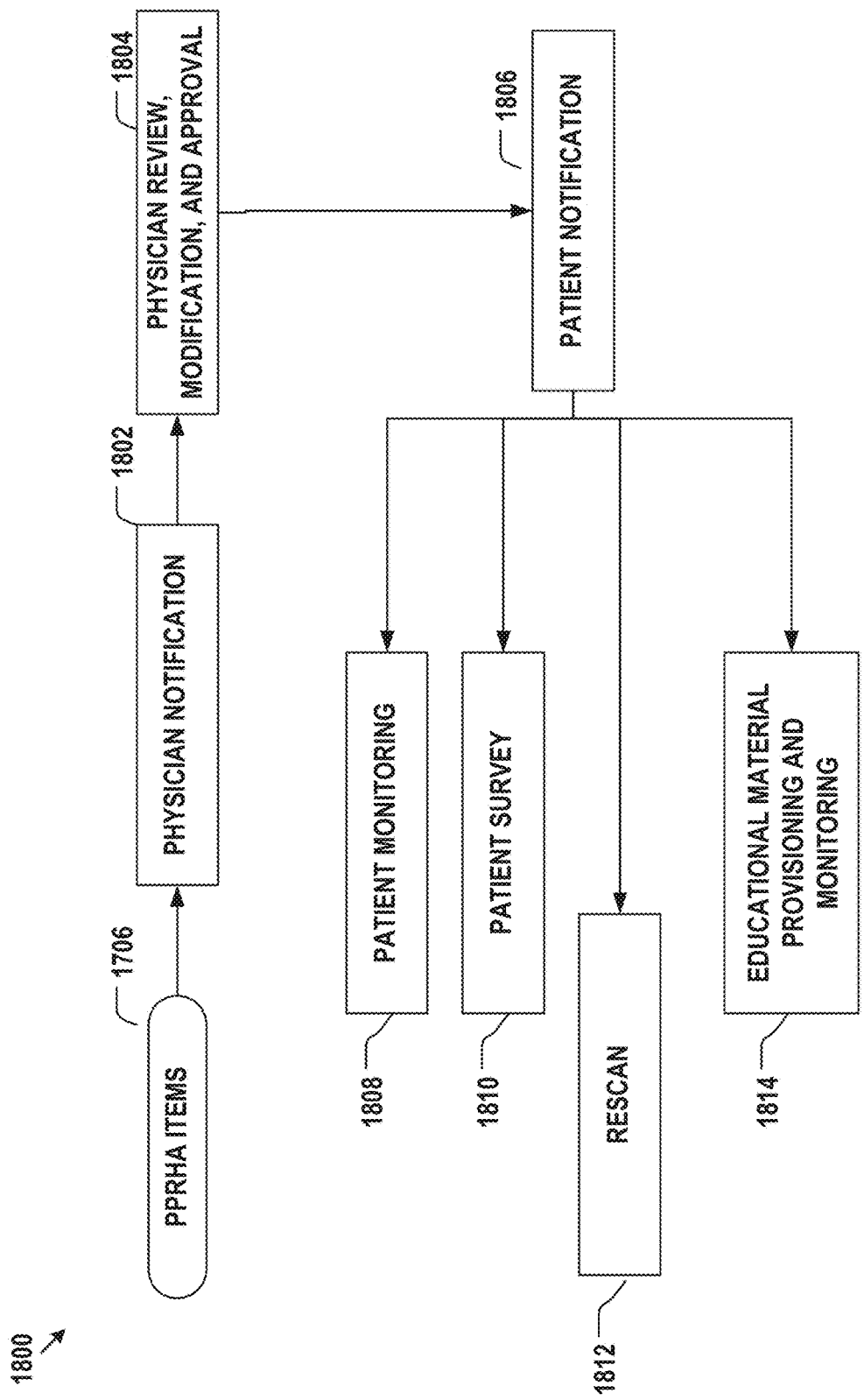
FIG. 18 shows an exemplary post-advocacy data flow diagram with automatic monitoring of patient implementation of PPRHA items.

FIG. 18 further illustrates exemplary data workflow for post-diagnosis and post-advocacy monitoring and tracking 1800. In one embodiment, the PPRHA items 1706 generated by the intelligent PPRHA model and engine 1704 of FIG. 17 (or 216 of FIG. 2) may be delivered by the portal server 102 of FIG. 1 to the physician terminal device (118 of FIG. 1) via the physician notification process 1802. Automatically generated PPRHA items 1706 may be subject to physician modification and approval (1804). As such, the physician terminal device 118 may be provided with one or more applications for performing notification, modification, approval and other functions. Graphical user interfaces may be provided via the applications. Exemplary embodiments of the graphical user interfaces will be shown below with respect to FIGS. 20-27.

The PPRHA approved and/or modified by the physician may then be delivered to the patient terminal device (122 of FIG. 1) via the portal server 102 and a patient notification process 1806. The patient terminal device may be installed with a monitoring and tracking application which communicates with the portal server and performs functions including but not limited to a patient monitoring function 1808, a patient survey function 1810, and an educational material provisioning and monitoring function 1814. The patient monitoring function 1808, for example, may provide tracking of user implementation of the PPRHA items 1706 (e.g., physical therapeutic exercises prescribed for postural conditions). The patient survey function 1810 may provide periodic patient or other voluntary feedback from the patient describing their body condition and perceived effectiveness of the PPRHA items 1706 as the PPRHA items are being implemented. The educational material provisioning and monitoring function 1814 may provide educational information about the PPRHA items 1706 to help the patient to implement the PPRHA items. For example, demo videos may be provided to the patient to guide the patient through a particular physical therapeutic exercise as part of the PPRHA item. The utilization of the educational material may be further tracked by the patient terminal device and reported to the portal server. Patient monitoring and tracking functions may be provided on the patient terminal devices via one or more graphical user interfaces. Exemplary embodiment of the graphical user interfaces will be further described with respect to FIGS. 28-30 below.

Continuing with FIG. 18, the post-diagnosis and post-advocacy monitoring may further include data recollection (e.g., rescan) 1812 of the patient using any of the distributed data collection devices 104 and 106 of FIG. 1. Data recollection may be performed periodically or at any selected time during or after patient implementation of the PPRHA items. The recollected data may be analyzed following data workflow that are similar to those used for the original data as illustrated in, e.g., FIG. 2. The purpose of the data recollection, for example, is for accessing effectiveness of the PPRHA items 1706 and for improving the intelligent PPRHA model and engine 1704 of FIG. 17.

Figure 19:
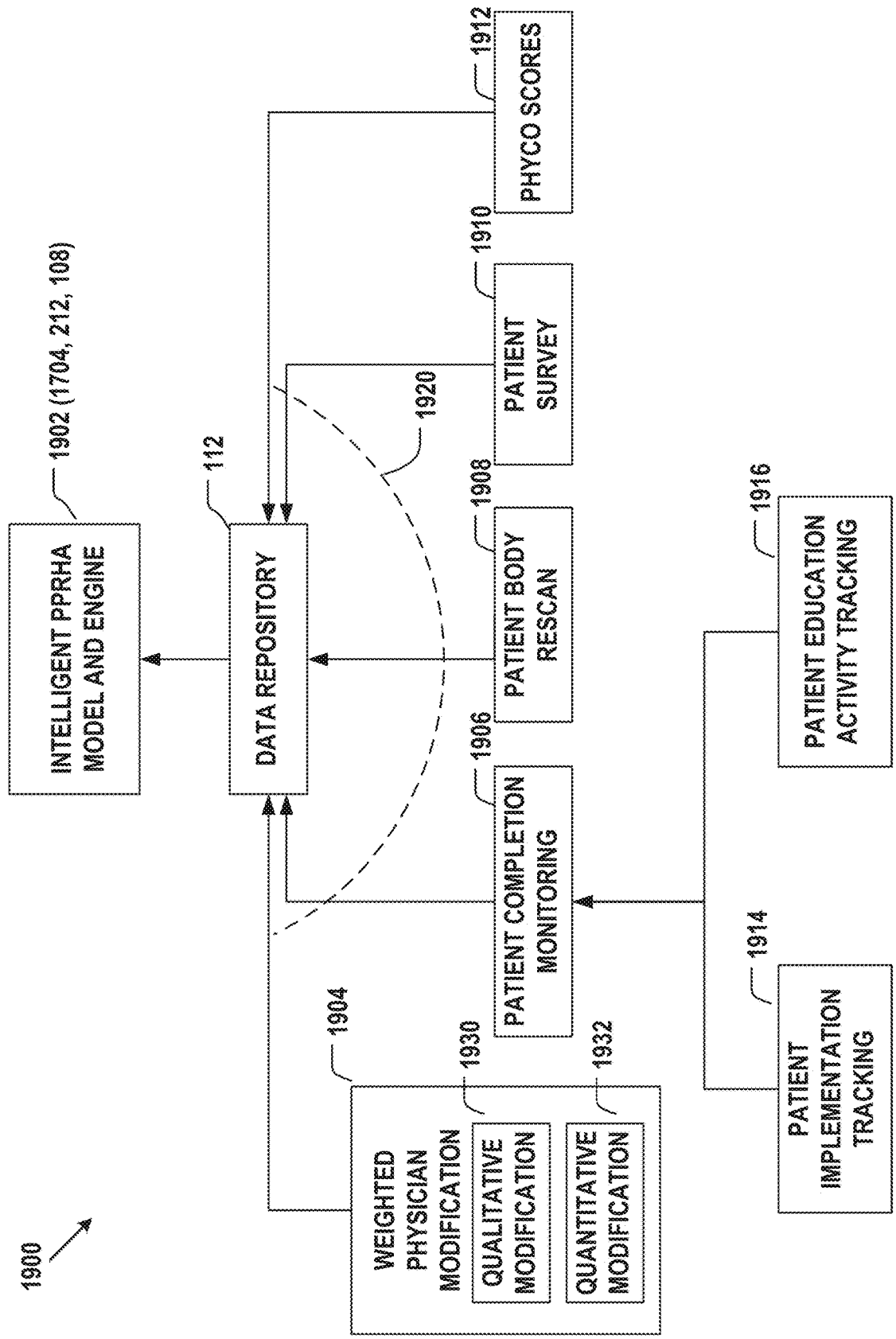
FIG. 19 illustrates various optional weighted feedback paths and data workflow into the intelligent PPRHA engine of FIGS. 1, 2, and 17.

FIG. 19 illustrates an exemplary embodiment for improving the intelligent PPRHA model 1902 (or 1704 of FIG. 17, or 212 of FIG. 2) via multiple feedback paths along the arrows indicated by 1920. Multiple feedback may be weighted using a predetermined set of weight parameters. The multiple feedback paths may include but are not limited to physician modification of the PPRHA items 1904, monitored status of patient implementation and completion of the PPRHA items 1906, patient body rescan 1908 (see description above with respect to element 1812 of FIG. 18), patient survey 1910, and PHYCO scores 1912, patient survey 1910, patient body rescan 1908, as the data are updated. Data may be maintained in the data repository 112 with time stamps. Historical feedback data, for example, may be used as input, in addition to the PHC vector indicated in FIG. 17 for performing updated training of the intelligent PPRHA model and engine 1902. In some embodiments, the intelligent PPRHA model 1902 may be trained and updated periodically based on additional new feedback data that becomes available (to the historical data maintained by the data repository 112) after a previous training of the intelligent PPRHA model. As such, the intelligent PPRHA model 1902 can be updated and improved as it is being used and as more data is collected and stored in the data repository 112.

In some embodiments, the feedback path via patient monitoring 1906 in FIG. 19 may include but are not limited to tracking of patient implementation of the PPRHA items (1914) and the tracking of patient utilization of the educational materials (1916) described above. In particular, determination as to whether the patient has rigorously implemented the PPRHA items and whether the patient has followed the instructions from the educational materials may be correlated with and impact actual effectiveness of the PPRHA Items. This information may be taken into consideration in the training of the intelligent PPRHA model 1902 such that the model would be less likely to treat a PPRHA item as ineffective when it does not improve patient health at least partially because the patient has not rigorously followed the PPRHA items and/or has not implemented the PPRHA items correctly.

In some embodiments, the feedback path via the physician modification tracking 1904 may further include tracking the type of modification made by the physician. In particular, a physician, after viewing the patient data and the data automatically provided by the intelligent PPRHA model 1902, may decide to modify the PPRHA item in different manners. For example, the physician may add or remove a PPRHA component (qualitative modification 1930). For another example, the physician may keep a PPRHA component, but modify the amount and/or implementation frequency of the PPRHA component (quantitative modification 1932). Different types of modification may be recorded by the physician terminal device and reported to the intelligent PPRHA engine (108 of FIG. 1) via the portal server (102 of FIG. 1). Data sets may be weighted differently for improving the intelligent PPRHA model 1902 via, e.g., periodic retraining.

FIGS. 20-27 illustrate exemplary graphical user interfaces for the physician terminal device 118 of FIG. 1 for implementing the various physician functions (see, e.g., 1804 of FIG. 18). The graphical user interfaces may be provided via one or more application(s) running on the physician terminal device.

Figure 20:
Figure 21:
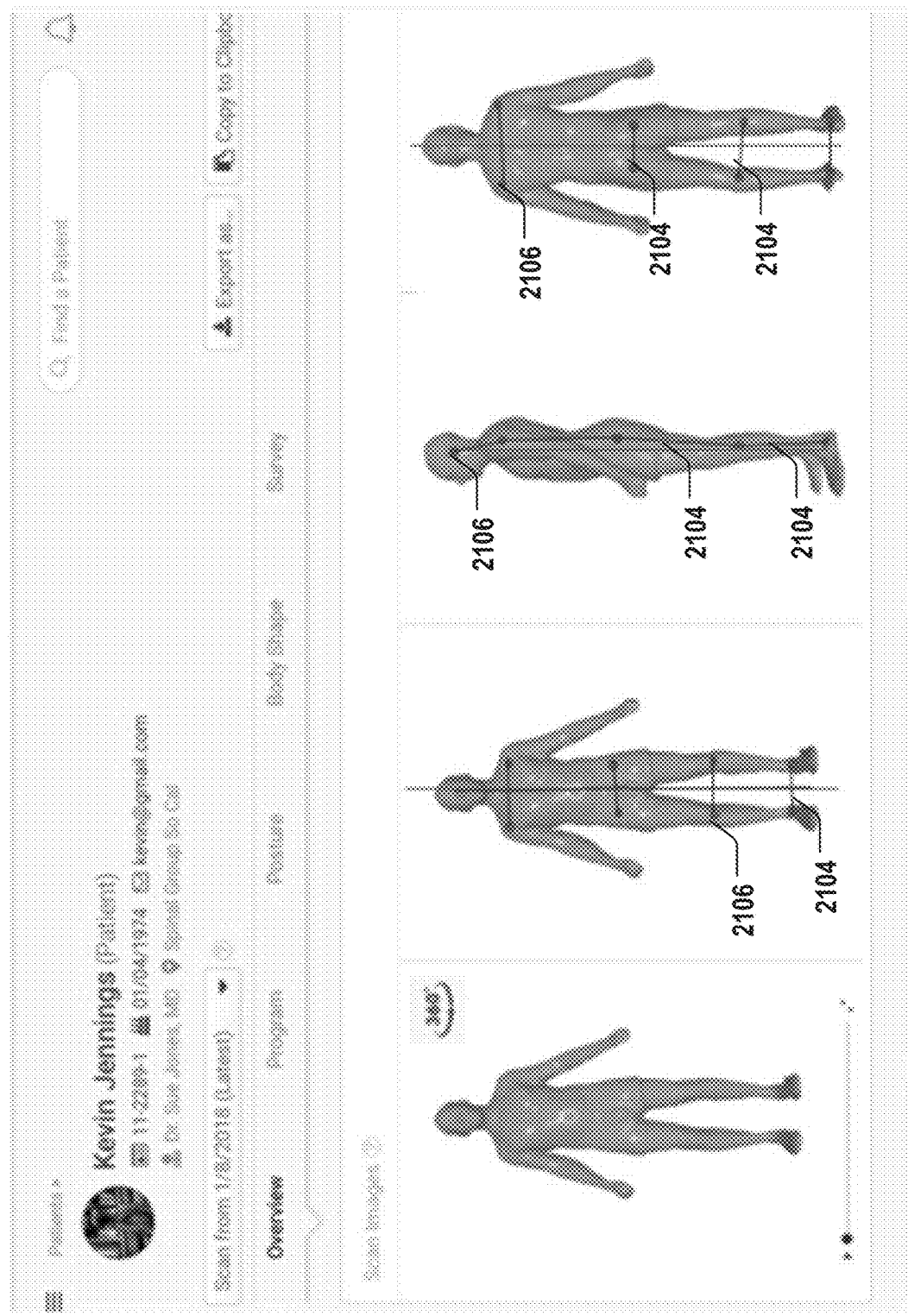

FIG. 20, for example, illustrates an exemplary graphical user interface for notifying physician of patients where PPRHA items (e.g., therapeutic programs) require review and approval. The patient list 2004 and their programs 2006 may be listed in multiple scrollable pages as shown by 2002. Each listed patient in the patient list 2004 and programs 2006 may be linked to further content for physician review. The physician may choose to approve one or more or all of the programs using the button and check boxes 2008.

Figure 22:
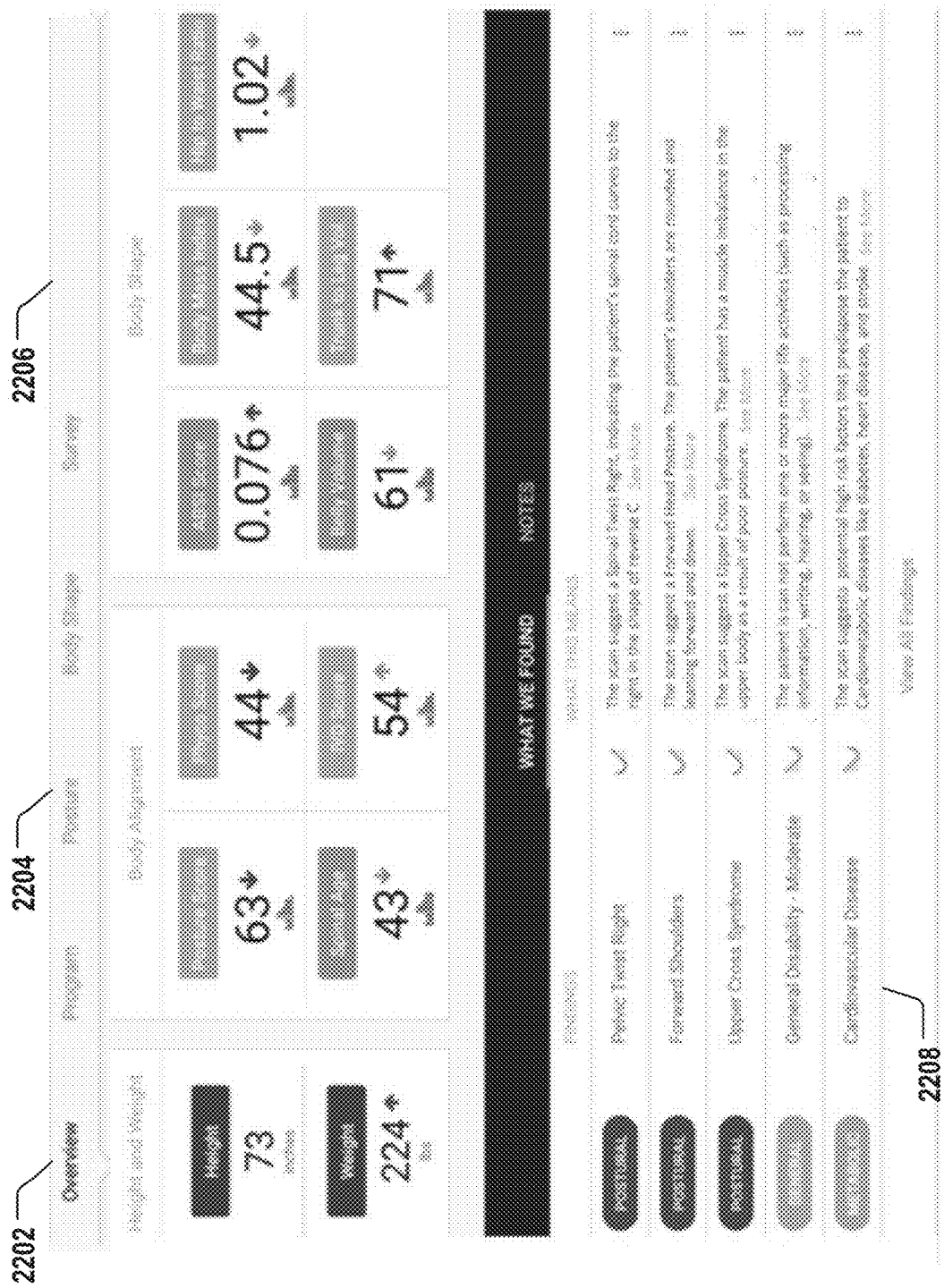
Figure 23:
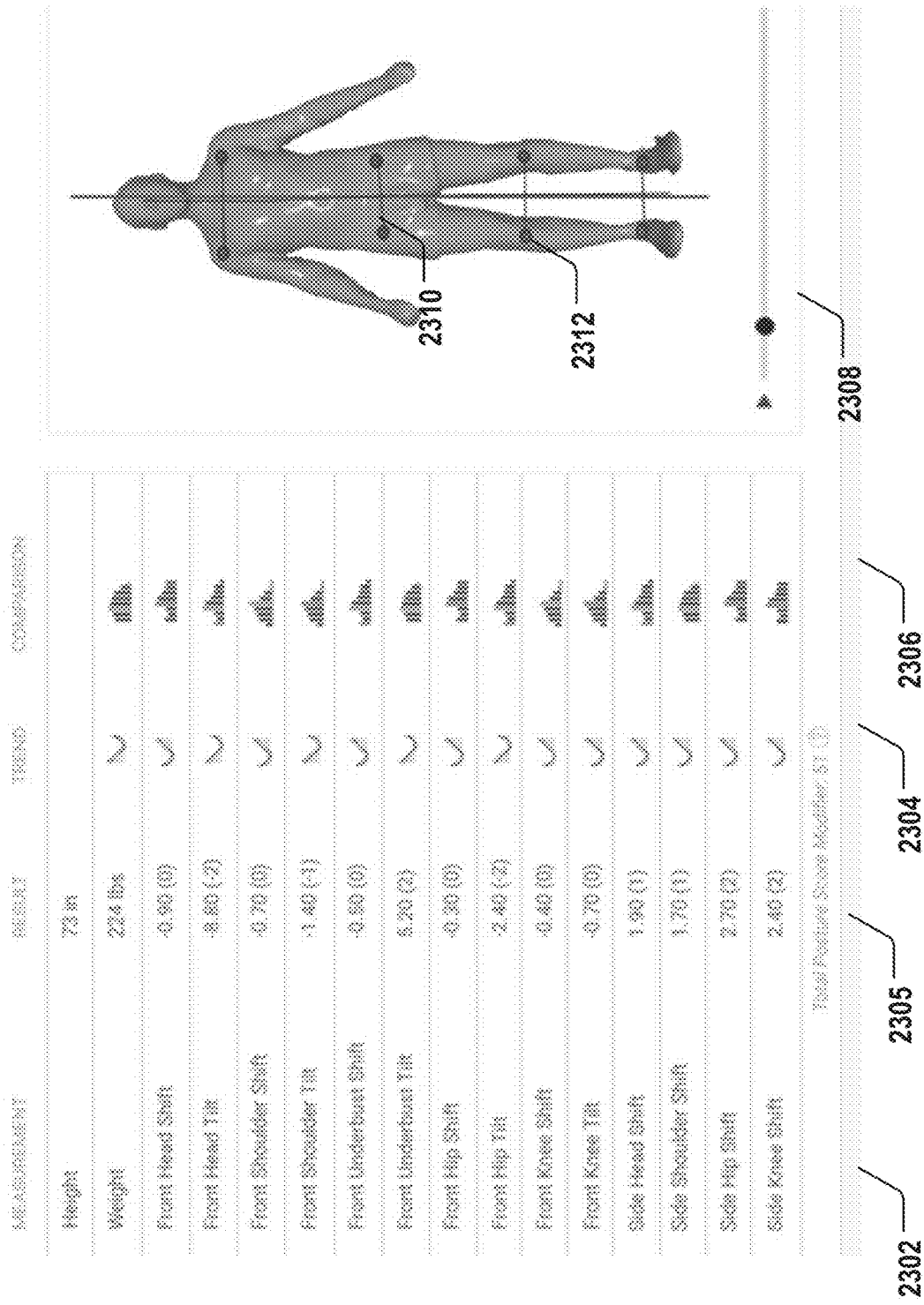

FIGS. 21-24 illustrate exemplary graphical user interfaces for physician review of patient data. The user interface in FIG. 21, for example, provides a graphical view of patient posture 2102 with various guiding lines 2104 and reference points 2106. FIG. 22, as another example, provides a graphical user interface depicting height/weight (2202), body alignment (2204), body shape (2206) data, and general findings by the PHCI engine (2208). FIG. 23, for example, provides a graphical user interface for the physician to view various postural tilt and shift components 2302 of the health indicator vector 540 of FIG. 11. In this example, results 2305 of various postural tilt and shift components 2302 are shown. Column 2304 shows a historical trend of tracked components for the patient. Column 2306 shows individual patient data compared to a group of patients with respect to each of the postural tilt and shift components. Historical evolution of postural tilts and shifts of the patient may also be shown as, e.g., an animation clip 2308 with various guidelines and reference points, such as 2310 and 2312. FIG. 24 shows a graphical user interface for providing details of other results 2404 for various measurements 2402 that may be obtained from the 3D body scan data, with historical trend information 2406 and comparison to others 2408.

Figure 25:
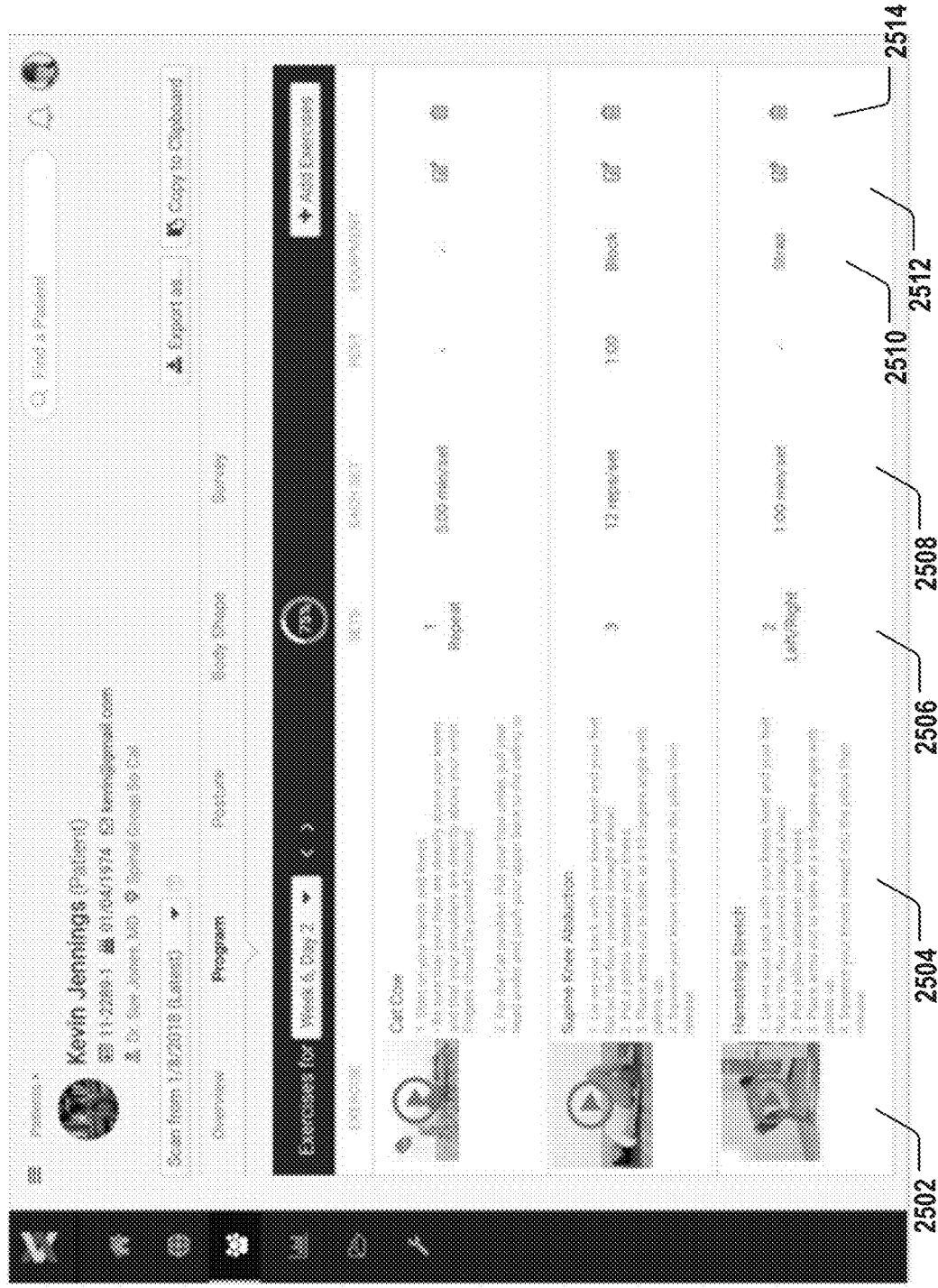

FIG. 25 illustrates an exemplary graphical user interface for showing PPRHA details for an individual patient. The example is provided in the context of physical therapy exercise programs. Column 2502 shows links to demo videos to particular prescribed exercises 2504. Column 2506 shows prescribed quantity for the exercise in terms of number of sets. Column 2508 shows prescribed strenuous level of the exercise in terms of completion duration, number of repetitions, and other quantities for each exercise set. Column 2510 lists equipment needed for the exercises. The edit button in column 2512 allows the physician to modify the exercise in terms of, e.g., quantity and strenuous level for each prescribed exercise. Buttons in column 2514 allow the physician to remove one or more of the prescribed exercises.

Figure 26:

FIG. 26 illustrates an exemplary graphical user interface for the physician to add videos listed in 2602 and corresponding exercises listed in 2604 using the check boxes 2612 to the PPRHA generated by the intelligent PPRHA model. The physician may further provide quantity 2606, duration 2610, and weight-bearings 2608 (if application) for the added exercises.

Figure 27:
Figure 28:
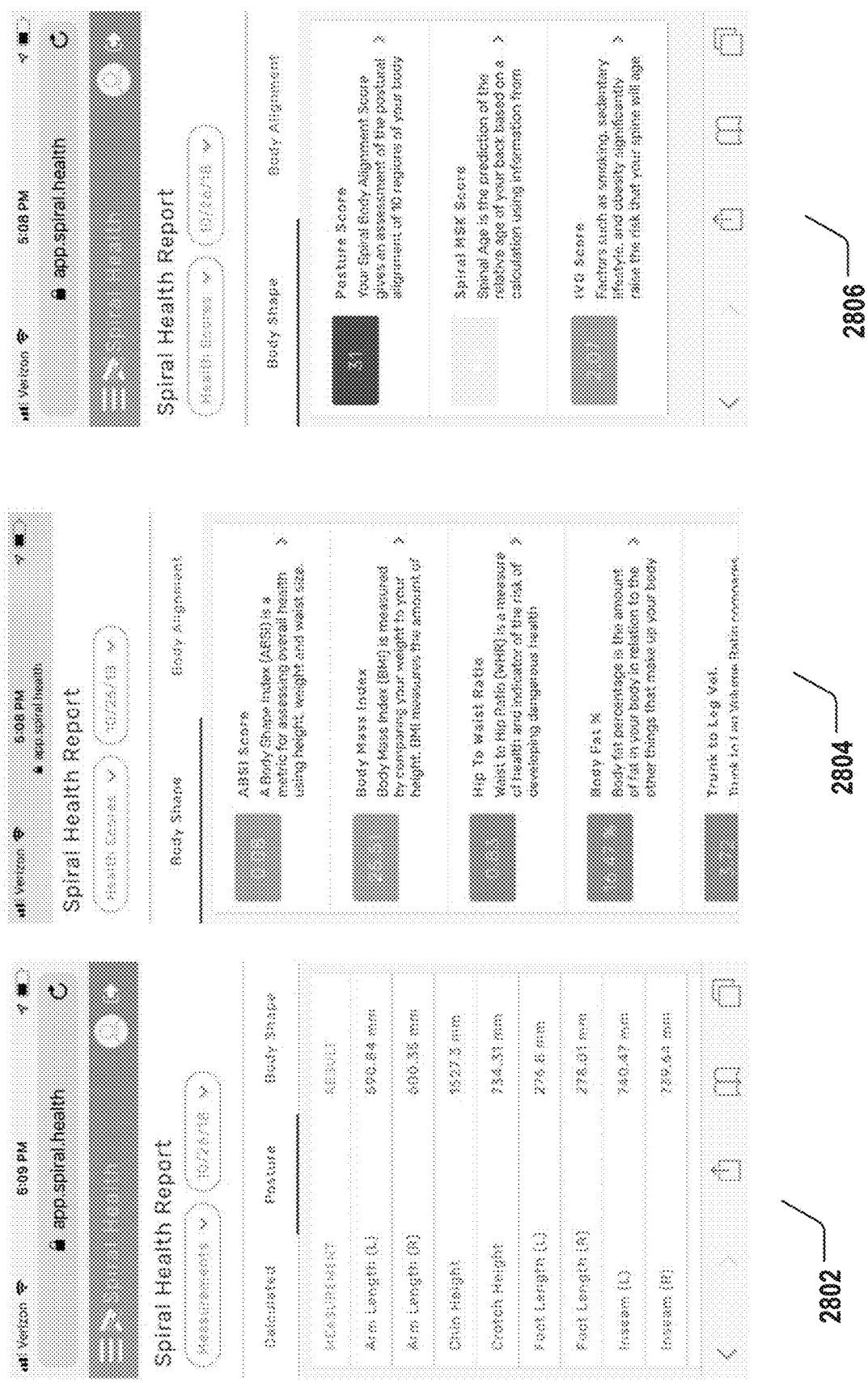
Figure 29:
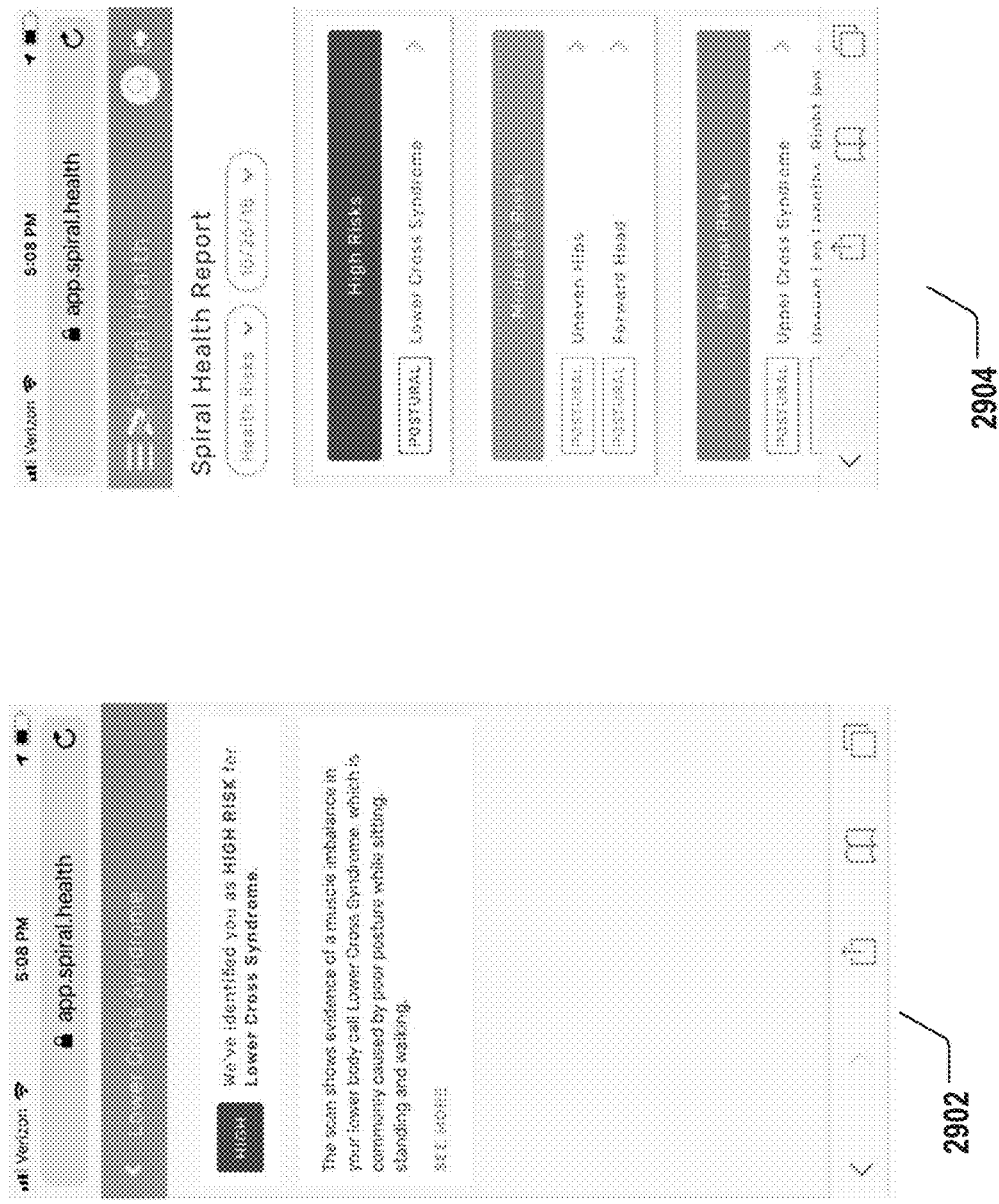
Figure 31:
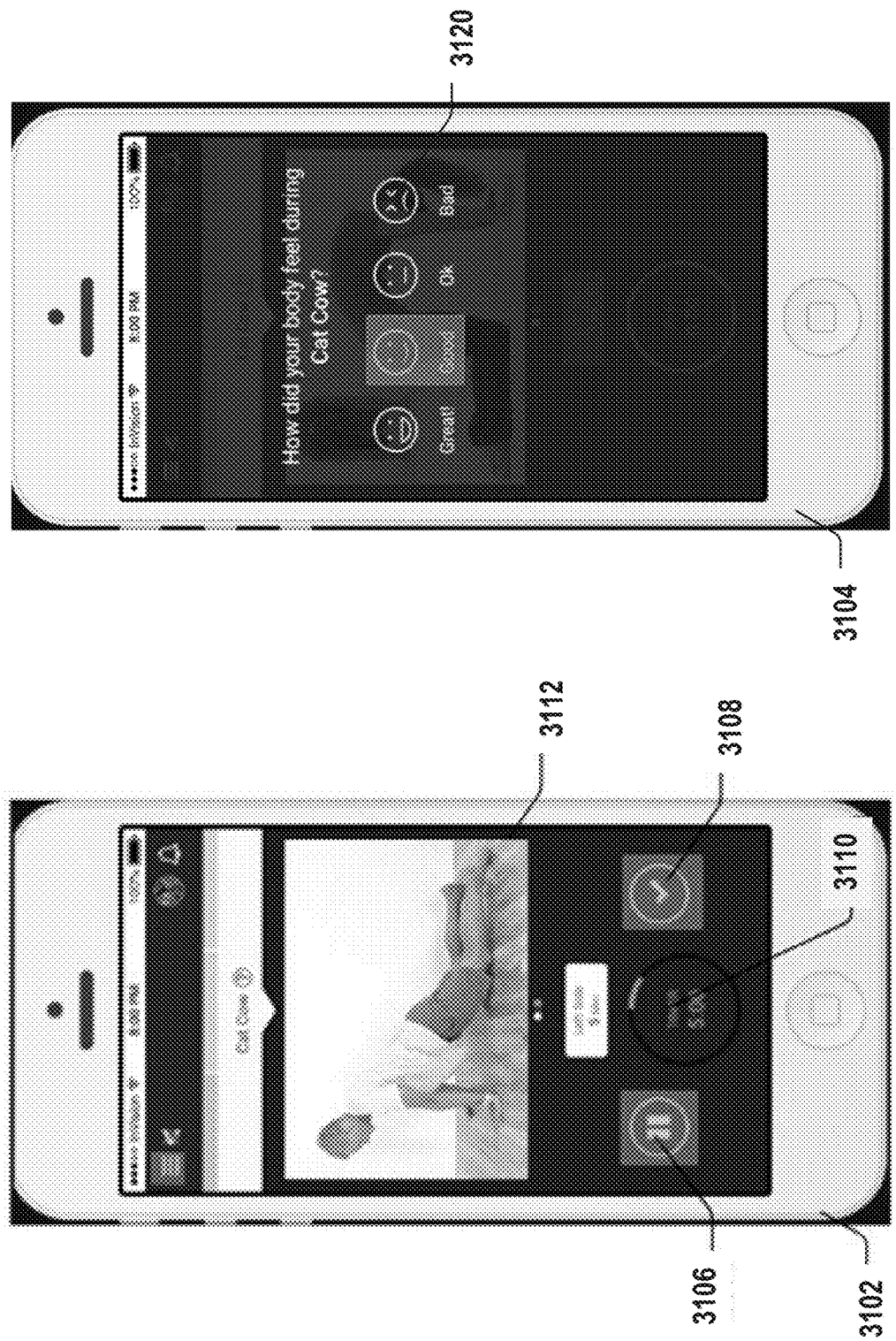

FIGS. 27-31 illustrate exemplary graphical user interfaces for the patient terminal device 122 of FIG. 1 for implementing the various patient tracking and monitoring functions (see, e.g., 1808, 1810, and 1814 of FIG. 18). For example, FIG. 27 shows graphical user interfaces for displaying pre-scan survey (2702), for patient notification of 3D body scan data availability (2704), for displaying postural visualization (2706) to the patient, similar to the graphical user interfaces for the physician in FIG. 21. FIG. 28, for another example, shows graphical user interface for displaying postural parameters (2802), body shape parameters (2804), and over all postural and IVD scores (2806), similar to the graphical user interface for the physician shown in FIG. 22. For another example, FIG. 29 shows exemplary graphical user interfaces 2902 and 2904 for displaying various postural risks for the patient in, e.g., high and moderate categories. FIG. 30 further shows a graphical user interface 3002 for showing a visual ergonomic assessment for the patient and a graphical user interface 3004 for showing educational material such as videos. For yet another example, FIG. 31 shows a graphical user interface 3102 for tracking patient implementation of the PPRHA items. For example, the patient may track exercises using the toggling play/pause button 3106 and complete button 3108. The time progression of the exercise may be shown by 3110. The graphical user interface 3102 may further show demo video 3112 during the exercise. FIG. 31 further shows another exemplary graphical user interface 3104 for taking patient survey during or after the exercise by providing selectable survey options 3120 to the user. As discussed above, the information tracked by the patient terminal devices via the graphical user interfaces 3102 and 3104 may be recorded and communicated to the portal server and used by the intelligent PPRHA engine to improve the PPRHA model.

Figure 32:
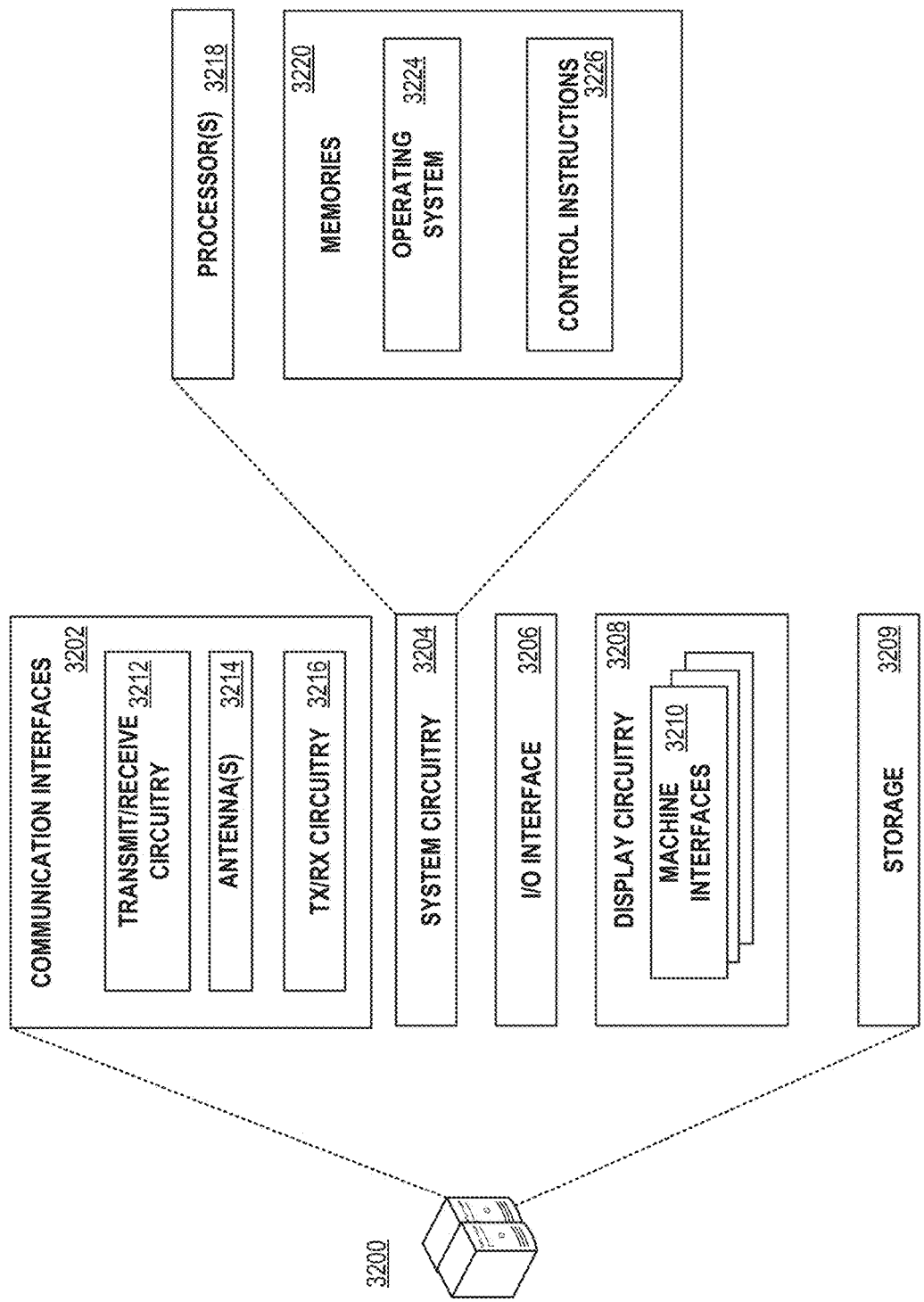
FIG. 32 shows an exemplary hardware composition of various processing engines, servers, and terminal devices of the distributed data processing system of FIG. 1.

The computing resources and components for supporting the functioning of the various terminals and servers of the system in FIG. 1 may be based on the computer system 3200 shown in FIG. 32. The computer system 3200 may include communication interfaces 3202, system circuitry 3204, input/output (I/O) interfaces 3206, storage 3209, and display circuitry 3208 that generates machine interfaces 3210 locally or for remote display, e.g., in a web browser or other applications running on a local or remote machine. The machine interfaces 3210 and the I/O interfaces 3206 may include graphical user interfaces (GUIs), touch sensitive displays, voice or facial recognition inputs, buttons, switches, speakers and other user interface elements. Additional examples of the I/O interfaces 3206 include microphones, video and still image cameras, headset and microphone input/output jacks, Universal Serial Bus (USB) connectors, memory card slots, and other types of inputs. The I/O interfaces 3206 may further include magnetic or optical media interfaces (e.g., a CDROM or DVD drive), serial and parallel bus interfaces, and keyboard and mouse interfaces.

The communication interfaces 3202 may include wireless transmitters and receivers ("transceivers") 3212 and any antennas 3214 used by the transmitting and receiving circuitry of the transceivers 3212. The transceivers 3212 and antennas 3214 may support Wi-Fi network communications, for instance, under any version of IEEE 802.11, e.g., 802.11n or 802.11ac. The communication interfaces 3202 may also include wireline transceivers 3216. The wireline transceivers 3216 may provide physical layer interfaces for any of a wide range of communication protocols, such as any type of Ethernet, data over cable service interface specification (DOCSIS), digital subscriber line (DSL), Synchronous Optical Network (SONET), or other protocol.

The storage 3209 may be used to store various initial, intermediate, or final datasets or models needed for the intelligent screening, PHCI, PPRHA and monitoring system. The storage 3209 may be centralized or distributed, and may be local or remote to the computer system 3200.

The system circuitry 3204 may include hardware, software, firmware, or other circuitry in any combination. The system circuitry 3204 may be implemented, for example, with one or more systems on a chip (SoC), application specific integrated circuits (ASIC), microprocessors, discrete analog and digital circuits, and other circuitry. The system circuitry 3204 is part of the implementation of any desired functionality related system 100 of FIG. 1. As just one example, the system circuitry 3204 may include one or more instruction processors 3218 and memories 3220. The memories 3220 stores, for example, control instructions 3226 and an operating system 3224. In one embodiment, the instruction processors 3218 executes the control instructions 3226 and the operating system 3224 to carry out any desired functionality related to the system 100 of FIG. 1.

Figure 35:
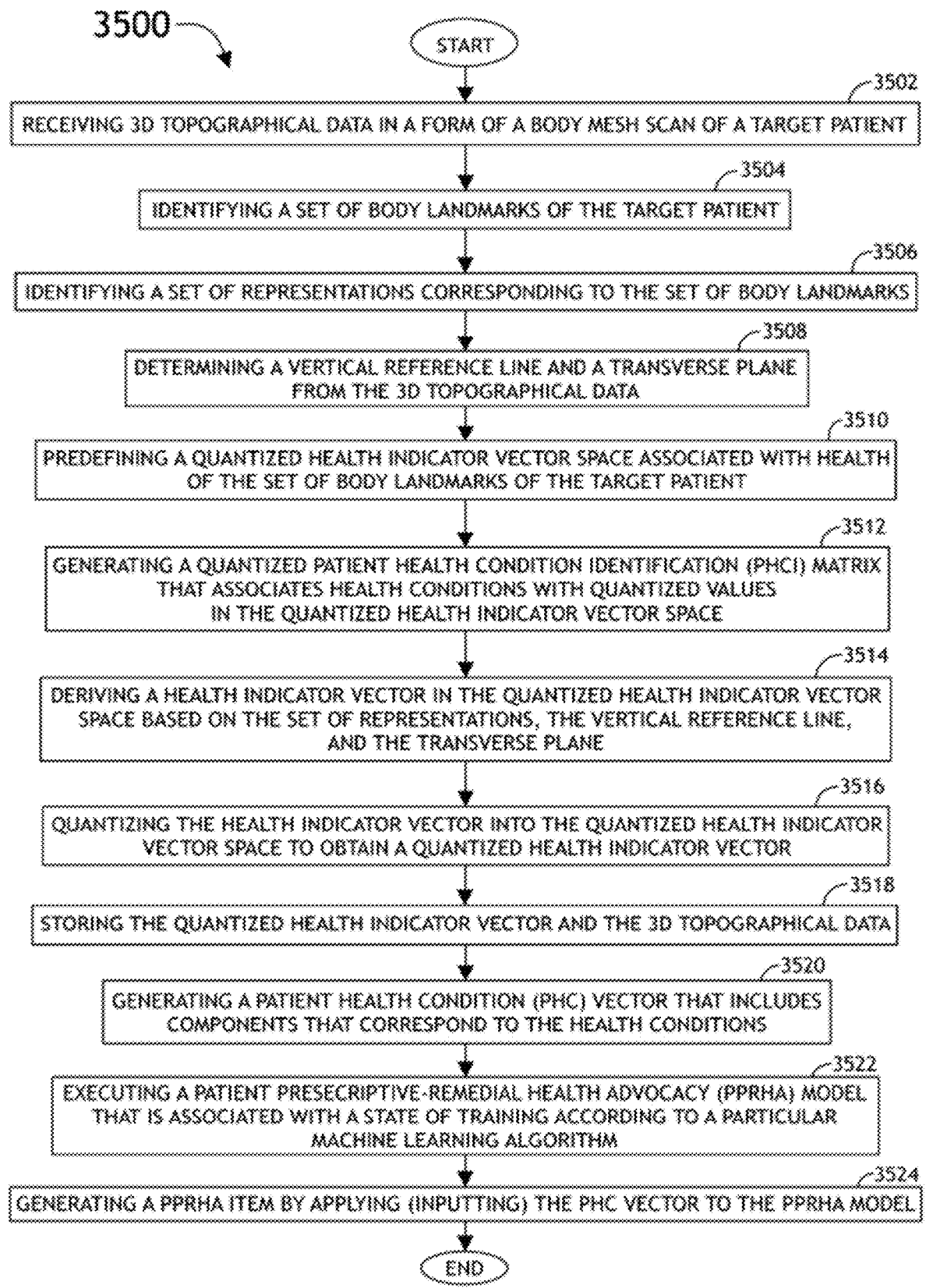
FIG. 35 shows an exemplary logic flow for automatic and intelligent PHCI and PPRHA.

Finally, by way of example, FIG. 35 conceptually illustrates a method 3500 for automatic and intelligent PHCI and PPRHA. In some embodiments, the method 3500 for automatic and intelligent PHCI and PPRHA is implemented as one or more software programs, modules, components, plug-ins, or applications which run on at least one processing unit of a computing device. For example, software that implements the method 3500 for automatic and intelligent PHCI and PPRHA may run on a patient health data (PHD) collection device (such as PHD collection device 104 or 106 described above by reference to FIG. 1), a physician terminal device (such as physician terminal device 118 described above by reference to FIG. 1), a tracking terminal device (such as tracking terminal device 122 described above by reference to FIG. 1), the intelligent PHCI engine 114 and/or the intelligent PPRHA engine 108 (both described above by reference to FIG. 1), and/or one or more portal server(s) (such as portal server 102 described above by reference to FIG. 1).

In some embodiments, the method 3500 for automatic and intelligent PHCI and PPRHA starts by receiving (at 3502) three-dimensional topographical data in a form of a body mesh scan of a target patient. Such topographical data may be collected by PHD devices 104 of FIG. 1.

In some embodiments, the method 3500 for automatic and intelligent PHCI and PPRHA then identifies (at 3504) a set of body landmarks of the target patient by performing data analytics on the three-dimensional topographical data taken from the PHD devices. The data analytics may be based on image and pattern recognition of particular body segments. Position and/or orientation of these body segments may be indicative of postural conditions of the target patient.

Next, the method 3500 for automatic and intelligent PHCI and PPRHA identifies (at 3506) a set of representations corresponding to the set of body landmarks. For examples, the body landmarks may be represented by a single points, by multiple points, a line, and the like. The set of representations for the set of body landmark may indicate postural conditions of the target patient.

Next, the method 3500 for automatic and intelligent PHCI and PPRHA determines (at 3508) a vertical reference line and transverse plane form the 3D topographical data. The vertical reference line and transverse plane may be determined using a force distribution measured by a force plate in conjunction with the PHD collection device.

In some embodiments, the method 3500 for automatic and intelligent PHCI and PPRHA then predefines (at 3510) a quantized health indicator vector space associated with health of the set of body landmarks of the target patient. The health indicator vector space may include components carrying information relevant to a determination of patient health conditions. The vector components may be defined as having quantized values.

In some embodiments, the method 3500 for automatic and intelligent PHCI and PPRHA generates (at 3512) a quantized PHCI matrix that associates health conditions with quantized values in the quantized health indicator vector space. After generating the quantized PHCI matrix, the method 3500 for automatic and intelligent PHCI and PPRHA derives (at 3514) a health indicator vector in the quantized health indicator vector space based on the set of representations, the vertical reference line, and the transverse plane. For example, the set of representations, the vertical reference line, and the transverse plane may be used to derive various postural deviations, which may form the various components of the health indicator vector mapped to the health indicator vector space. Next, the method 3500 for automatic and intelligent PHCI and PPRHA quantizes (at 3516) the health indicator vector into the quantized health indicator vector space to obtain a quantized health indicator vector. After quantization, the method 3500 for automatic and intelligent PHCI and PPRHA stores (at 3518) the quantized health indicator vector and the 3D topographical data.

In some embodiments, the method 3500 for automatic and intelligent PHCI and PPRHA generates (at 3520) a PHC vector that includes components that correspond to the health conditions based on the quantized health indicator vector and the PHCI matrix.

After generation of the PHC vector, the method 3500 for automatic and intelligent PHCI and PPRHA executes (at 3522) a PPRHA model that is associated with a state of training according to a particular machine learning algorithm and then generates (at 3524) one or more PPRHA items by applying or inputting the PHC vector to the PPRHA model. The PPRHA items may be provided to the physician or patient to follow. After generating the one or more PPRHA items, the method 3500 for automatic and intelligent PHCI and PPRHA ends.

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in tangible storage media that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on other machine-readable media. The media may be made-up of a single (e.g., unitary) storage device, multiple storage devices, a distributed storage device, or other storage configuration. A product, such as a computer program product, may include storage media and instructions stored in or on the media, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

Various embodiments have been specifically described. However, many other embodiments are also possible.

What is claimed is:

1. A system for automatic and intelligent patient health condition identification (PHCI) and patient preventive/remedial health advocacy (PPRHA), comprising:
   a scanning platform having a plurality of optical sensors and a force plate;
   a data repository;
   a communication interface; and
   processing circuitry in communication with the scanning platform, the data repository and the communication interface, wherein the processing circuitry is configured to:
   receive body topography data for a target patient from the plurality of optical sensors via the communication interface;
   receive force data from the force plate via the communication interface;
   execute a data segmentation model trained based on a first machine learning algorithm to automatically identify a predetermined set of body landmarks of the target patient and identify a set of representations corresponding to the predetermined set of body landmarks of the target patient;
   associate each of a plurality of predetermined health conditions with quantized values in a quantized health indicator vector space to generate a quantized PHCI matrix;
   derive a health indicator vector in the quantized health indicator vector space based on the set of representations and the force data;
   quantize the health indicator vector into the quantized health indicator vector space to obtain a quantized health indicator vector;
   store the quantized health indicator vector and data from the scanning platform in the data repository;
   automatically generate a patient health condition (PHC) vector comprising a plurality of components each corresponding to one of the plurality of predetermined health conditions; and
   automatically generate a PPRHA item from the PHC vector using a PPRHA model trained by a second machine learning algorithm.

2. The system of claim 1, wherein:
the quantized health indicator vector space comprises dimensions associated with balancing characteristics derived from the predetermined set of body landmarks and force data of the target patient; and
the PHC vector comprises a binary PHC vector comprising dimensions each represented by a binary value.

3. The system of claim 2, wherein:
the processing circuitry is configured to derive static balancing characteristics from a single snapshot of the body topography data and the force data.

4. The system of claim 2, wherein:
the processing circuitry is configured to derive dynamic balancing characteristics from multiple snapshots taken over time of the body topography data and the force data.

5. The system of claim 4, wherein the dynamic balancing characteristics comprise body sway of the target patient and the processing circuitry is configured to determine the body sway based on variations of force distribution in the force data over time.

6. The system of claim 2, wherein:
the quantized health indicator vector space comprises dimensions associated with tilt deviations and shift deviations in front-view and shift deviations in side-view of the predetermined set of body landmarks of the target patient;
the predetermined set of body landmarks of the target patient comprises head, hips, shoulders, knees, and underbusts; and
wherein the tilt deviations and shift deviations in front-view comprises a head shift, a head tilt, a shoulder shift, a shoulder tilt, an underbust shift, an underbust tilt, a hip shift, a hip tilt, a knee shift, and a knee tilt.

7. The system of claim 1, wherein the set of representations comprises at least one circumferential attribute.

8. The system of claim 7, wherein the at least one circumferential attribute comprises circumferences of two body landmarks among the predetermined set of body landmarks of the target patient, and wherein the quantized health indicator vector space comprises at least a dimension representing a quantized ratio between the circumferences of the two body landmarks.

9. The system of claim 1, further comprising a portal server for providing a first graphical user interface to a patient terminal device for displaying the PPRHA item to the target patient.

10. The system of claim 1, further comprising a portal server for providing a second graphical user interface to a physician terminal device, wherein:
the second graphical user interface is configured to display the PPRHA item in the physician terminal device and to enable a physician to modify the PPRHA item to generate a modified PPRHA item; and
wherein the processing circuitry is further configured to record the modified PPRHA item in the data repository.

11. The system of claim 10, wherein the portal server is further configured to provide a first graphical user interface to a patient terminal device for displaying the modified PPRHA item to the target patient.

12. The system of claim 11, wherein:
the PPRHA item comprises a therapeutic exercise and the modified PPRHA item comprises a modified therapeutic exercise; and
the first graphical user interface is further configured to provide monitoring functions for tracking execution of the modified therapeutic exercise by the target patient.

13. The system of claim 12, wherein the first graphical user interface comprises clickable buttons for the target patient to report execution of the modified therapeutic exercise.

14. The system of claim 13, wherein the data repository further stores demo videos and wherein the first graphical user interface is configured to provide option to select and play demo videos corresponding to the modified therapeutic exercise.

15. A method for automatic and intelligent patient health condition identification (PHCI) and patient preventive/remedial health advocacy (PPRHA) by processing circuitry in communication with a data repository and a communication interface, comprising:
receiving body topography data in a form of body mesh scan of a target patient from one of a plurality of distributed optical sensors via the communication interface;
receiving force data from a force plate positioned under the target patient via the communication interface;
executing a data segmentation model trained based on a first machine learning algorithm to automatically identify a predetermined set of body landmarks of the target patient and identify a set of representations corresponding to the predetermined set of body landmarks of the target patient;
associating each of a plurality of predetermined health conditions with quantized values in a quantized health indicator vector space associated with health of the predetermined set of body landmarks of the target patient to generate a quantized PHCI matrix;
deriving a health indicator vector in the quantized health indicator vector space based on the set of representations and the force data
quantizing the health indicator vector into the quantized health indicator vector space to obtain a quantized health indicator vector;
storing the quantized health indicator vector and the body topography data in the data repository;
automatically generating a patient health condition (PHC) vector comprising a plurality of component each corresponding to one of the plurality of predetermined health conditions; and
automatically generating a PPRHA item from the PHC vector using a PPRHA model trained by a second machine learning algorithm.

16. The method of claim 15, wherein:
the quantized health indicator vector space comprises dimensions associated with balancing characteristics derived from the predetermined set of body landmarks and force data of the target patient; and
the PHC vector comprises a binary PHC vector comprising dimensions each represented by a binary value.

17. The method of claim 16, further comprising at least one of:
deriving static balancing characteristics from a single snapshot of the body topography data and the force data; or
deriving dynamic balancing characteristics from multiple snapshots taken over time of the body topography data and the force data.

18. The method of claim 17, wherein the dynamic balancing characteristics comprise body sway of the target patient and the method further comprises determining the body sway based on variations of force distribution in the force data over time.

19. The method of claim 15, wherein:
the PPRHA model is periodically retrained with updated training data based on a plurality of feedbacks; and
the PPRHA item comprises a therapeutic exercise.

20. The method of claim 19, wherein the plurality of feedbacks comprises:
modification of the therapeutic exercise by a physician as monitored by a portal server via a second graphical user interface on a physician terminal device;
self-evaluation following execution of the therapeutic exercise by the target patient as collected by the portal server via a first graphical user interface on a patient terminal device;
images or videos of the target patient taken by the patient terminal device while the target patient is executing the therapeutic exercise as reported to the portal server from the patient terminal device; or
records of viewing, by the target patient, demo videos provided to the patient terminal device via the first graphical user interface.

* * * * *